US006096872A

United States Patent [19]
Van Holten et al.

[11] Patent Number: 6,096,872
[45] Date of Patent: Aug. 1, 2000

[54] VIRAL CLEARANCE PROCESS

[75] Inventors: Robert William Van Holten, Flemington; Gilbert J. Quinton, Belle Meade, both of N.J.; George E. Oulundsen, Jr., Nashua, N.H.

[73] Assignees: Ortho Diagnostic Systems, Inc., Raritan, N.J.; Millipore Corporation, Bedford, Mass.

[21] Appl. No.: 08/950,157

[22] Filed: Oct. 14, 1997

[51] Int. Cl.$^7$ .......................... A61K 39/395; C07K 16/34
[52] U.S. Cl. ..................... 530/390.1; 424/173.1; 424/176.1; 530/389.6; 530/414
[58] Field of Search ................. 530/387.1, 414, 530/389.6, 390.1; 424/173.1, 176.1

[56] References Cited

U.S. PATENT DOCUMENTS

| | | | |
|---|---|---|---|
| 3,449,314 | 6/1969 | Pollack | 260/112 |
| 3,916,026 | 10/1975 | Stephan | 424/177 |
| 4,021,540 | 5/1977 | Pollack et al. | 424/86 |
| 4,141,887 | 2/1979 | Seufert | 260/112 B |
| 4,590,002 | 5/1986 | Zolton et al. | 530/386 |
| 4,880,913 | 11/1989 | Doleschel et al. | 530/387.1 |
| 5,115,101 | 5/1992 | Bloom et al. | 530/388.25 |
| 5,215,681 | 6/1993 | Truong et al. | 252/311 |
| 5,723,123 | 3/1998 | Karges et al. | 424/94.65 |

FOREIGN PATENT DOCUMENTS

| | | | |
|---|---|---|---|
| WO 96/00237 | 1/1996 | WIPO | C07K 1/34 |
| WO 98/08603 | 3/1998 | WIPO . | |

OTHER PUBLICATIONS

Van Holten, R.W. et al. Incorporation of a viral clearance step into a modified Cohn fractionation. Transfusion 35:13S, Oct. 1995.
Dorland's Illustrated Medical Dictionary, 28th Edition. W.B. Saunders Co. Philadelphia, 1994.
Hardy, R.R. Purification and characterization of monoclonal antibodies. Chapter 13 in Handbook of Experimental Immunology In Four Volumes. D.M. Weir, Editor. Blackwell Scientific Publications. Oxford. pp.13.1–13.13.
Ortho Diagnostic Systems Inc. MICRhoGAM TM and RhoGAM TM. in Physicians' Desk Reference. Medical Economics Data Production Co. Montvale, NJ. pp.1770–1771, 1995.
"Value of Virus Filtration as a Method for Improving the Safety of Plasma Products", Vox Sang 1995; 69:82–83.
"Size Exclusion Removal of Model Mammalian Viruses Using a Unique Membrane System, Part I: Membrane Qualification", Biologicals (1993) 21, 275–286.
"Removal of Causative Agent of Creutzfeldt–Jakob Disease (CJD) Through Membrane Filtration Method", Membrane, 18(6), 357–362 (1993).
"Preparation and Properties of Serum and Plasma Proteins. IV. A System for the Separation into Fractions of the Protein and Lipoprotein Components of Biological Tissues and Fluids", 1949, J. Am Chem. Soc. 68:459–475.
"Value of Virus Filtration as a Method for Improving the Safety of Plasmaa Products", Vox Sang, 1996; 70:235–236.
"The Separation of the Antibodies, Isoagglutinins, Prothrombin, Plasminogen and $\beta_1$—Lipoprotein into Subfractions of Human Plasma", Subfractions of Human Plasma, Feb. 1949 vol. 71, pp. 541–550.

Primary Examiner—David Saunders
Attorney, Agent, or Firm—Woodcock Washburn Kurtz Mackiewicz & Norris LLP

[57] ABSTRACT

Methods for producing immunoglobulins and in particular anti-D immunoglobulin substantially free of virus and product resulting therefrom. Specifically provided are methods for nanofiltration of the anti-D immunoglobulin in high ionic strength buffer and with excipient such as polysorbate 80. Additional steps include diafiltration to concentrate the anti-D protein and reduce the concentration of excipient present.

77 Claims, 6 Drawing Sheets

VIRAL CLEARANCE PROCESS

FIELD OF THE INVENTION

The field of the invention is the recovery of large proteinaceous material through a small pore exclusion filter during purification, viral reduction or viral clearance processing. Removal of virus by size exclusion from a large biomolecule such as a gamma globulin is generally hindered by the difficulty of efficiently passing a large globular protein through a size exclusion filter with the desirably small pore size necessitated for pharmaceutical and diagnostic use. The removal of virus from proteinaceous molecules using the processing methods of this invention results in a product substantially free of virus.

BACKGROUND OF THE INVENTION

The recovery of large proteinaceous material through a small pore exclusion filter during purification, viral reduction or viral clearance processing has posed significant problems for the pharmaceutical and diagnostic industry (see Roberts, P., Vox Sang, 1995;69:82–83). Removal of virus from a large biomolecule such as a gamma globulin (monoclonal or polyclonal) by size exclusion is hindered by the difficulty of efficiently passing a large globular protein through a size exclusion filter with a 12–15 nm pore size. The problem is especially evident where small non-enveloped virus are sought to be removed from products with high molecular weight. A further complication to the process is that proteinaceous materials such as immunoglobulins to be recovered form dimers and trimers, which pass through the filters with difficulty or not at all.

The smaller the membrane pore size the more effective the membrane is in retaining the viral particles. However, along with the smaller pore size comes a decrease in the ability of the membrane to allow the virally cleared product to freely pass through. As with all virus-reduction technologies each application must be assessed on its own merits for each product and each virus. In those cases where the removal of small non-enveloped viruses is required, the use of virus filters with the smallest pore size (less than 35 nm, and preferably between 12–30 nm) is probably essential and this may not be possible with products of high molecular weight, or with those that form dimers and trimers.

The problem is outlined in the publication of Roberts referenced hereinabove wherein it is discussed that while filters with nominal cutoff values of 70, 160 kD, and 15, 35, 40, 50 and 70 nm may be useful for removing small viruses and prions, products with larger molecular weights such as immunoglobulins (IgG, 150 kD) and factor VIII (350 kD) can only pass through filters of larger pore size.

The methods of the invention comprise the filtration processing and viral clearance of a pharmaceutical preparation of an immunoglobulin.

In the prevention of hemolytic disease of newborn the mother is injected with Rho(D) immunoglobulin of human origin. Such a product is RHOGAM® Rho(D) Immune Globulin (Human), available from the assignee hereof, and it operates by preventing the unimmunized Rho (D) negative mother from responding to Rho (D) antigen present on red cells and 'received' from an Rho(D) positive infant. Thus, by preventing anti-Rho (D) production by the mother, the subsequent Rho (D) positive infant of this mother is protected from hemolytic disease of the newborn. Although this successful product is presently produced by a Cohn alcohol fractionation type process, several investigators have attempted to use alternative methods to produce similar materials to thereby provide an economically more advantageous product, to reduce large plasma requirements. Such investigational efforts have been reported by Hoppe et al. in "Prevention of Rh Immunization Modified Production of IgG Anti-Rh For Intravenous Application By Ion Exchanged Chromatography", Vox Sang, 25:308–316 (1973) and Friesen et al. in "Column Ion-Exchange Preparation and Characterization of an Rh Immune Globulin for Intravenous Use", Journal of Applied Biochemistry, 3, 164–175 (1981).

Hoppe in Germany and Friesen in Canada both employed a DEAE-Sephadex chromatography column in conjunction with a phosphate buffer eluding agent. Hoppe's source of anti-D containing plasma was from volunteers who passed an HB Ag laboratory test for at least six months, the plasma being stored in the interim. Thus, Hoppe employed a relatively safe, noninfective plasma to start with. No additional tests were run, however, to determine the efficacy of the DEAE-Sephadex hepatitis B surface antigen. Hoppe's concern was instead directed towards the removal of aggregated materials and the isolation of an unfragmented, immunoeletrophoretically pure IgG having a relatively high antibody concentration. The Friesen publication reports on the modification's made to the Hoppe method for the development of an intravenous Rh IgG for use in Canada. As Hoppe had done, Friesen tested each unit of Rh plasma for HB AG to eliminate any donors testing positive. Friesen employed the radioimmunoassay kit from Abbott Laboratories, North Chicago, Ill. (Ausria I Kit). This test is still regarded as one of the most sensitive and was also employed in the development of the invention described later. Friesen reported that clinical trials showed the material produced using the DEAE Sephadex resin/phosphate buffer combination was effective and safe for the prevention of Rh immunization. Friesen, however, reported no additional tests for determining the efficacy of the DEAE-Sephadex/phosphate buffer combination for removing hepatitis B surface antigen from plasma samples. This, at least from the U.S. government's perspective, is especially important since the radioimmunoassay test employed in screening the donor plasma samples is incapable of detecting concentrations of HB AG particles two or three orders of magnitude lower which may still be infective. It is this concern for the potential infectivity of a reagent produced by such a method that the United States government has been significantly more restrictive in permitting the production of injectable immunoglobulin in reagents by solid phase methodologies.

RhoGAM® Rho(D) Immune Globulin (Human) was the first successful prophylactic use of specific antibody to achieve antibody mediated immune suppression. RHOGAM® Rho(D) Immune Globulin (Human) is an IgG immunoglobulin solution containing anti-Rho(D) at a dose of 300 micrograms of anti-D activity per dose. RHOGAM® Rho(D) Immune Globulin (Human) can be given to the nonimmunized, Rho(D) negative pregnant woman at the appropriate time prevent future disease in her Rho(D) positive offspring. The disease is called hemolytic disease of the newborn or more specifically, Rh-erythroblastosis fetalis.

A smaller dose of anti-Rho(D), MICRHOGAM® Rho(D) Immune Globulin (Human) (50 micrograms of anti-Rho(D)) is also sold by the Assignee hereof for treatment of women who have abortions and miscarriages at twelve weeks gestation or earlier. While the full dose protects the recipient for up to 15 ml of Rho(D) positive red cells, the smaller dose provides protection up to 2.5 ml of Rho(D) positive red cells. RHOGAM® Rho(D) Immune Globulin (Human) is used as antenatal prophylaxis at 26 to 28 weeks gestation. Other indications include threatened abortion at any stage of gestation with continuation of pregnancy, abortion or termination of pregnancy at or beyond 13 weeks gestation, abdominal trauma or genetic amniocentesis, chorionic villus sampling (CVS) and percutaneous umbilical blood sampling (PUBS).

Most immunoglobulin injectable materials approved for use by the FDA and Bureau of Biologics have been produced by the alcohol fractionation procedure developed by Dr. E. Cohn of Harvard during the 1940s and described in Cohn et al., J. Am. Chem. Soc. 68, 459 (1946), incorporated herein by reference. This procedure coupled with the careful selection of plasma negative for hepatitis infectivity, HIV, and other blood-borne pathogens determined by the most sensitive tests available, has been employed for such a long period of time that the US government has adopted a position favoring only the resultant preparation of this procedure as safe. That the products produced by this procedure are indeed safe can easily be demonstrated by the millions of non-infected recipients of product.

Several conventional methods for the separation of gamma globulin from human serum have been described notably for Baumstark et al. in "A Preparative Method For The Separation of 7S Gamma Globulin From Human Serum", Archives of Biochemistry and Biophysics, 108, 514–522 (1964) and by A. Webb in "A 30-Minute Preparative Method For Isolation Of IgG From Human Serum", Vox Sang, 23:279–290 (1972), both of which are incorporated herein by reference. Although both of these papers are more concerned with the separation and selection of various gamma globulin classes from a serum containing numerous other contaminating proteins, they do address the removal of contaminating proteins and materials from the original serum sample. Both employ a DEAE-Sephadex column chromatographic material with a phosphate buffer eluting agent. Both investigators met with some degree of success as far as removal of contaminating proteins was concerned, however, both failed to address the problem of removing contaminating hepatitis viral particles in order to provide a safe, injectable reagent.

It is an object of the instant invention to provide virally cleared, pure immunoglobulin for injection. Such a substantially pure product is produced using the processing methods of the invention.

It is a further object of this invention to provide a manufacturable process for purifying immunoglobulins which is reasonable in terms of temporal, square foot and protein yield requirements.

The filtration used in this invention is accomplished by a sieve-retention mechanism dependent upon the size relationship of the virus to the filter mean pore size. Its efficiency is not affected by filtration conditions of temperature, ionic strength, virus titer challenge, pressure, pH, surface tension, and other variables. While affecting the ability of the IgG particle to pass through the filter, the detergent and ionic strength conditions of the invention do not affect the viral clearance. Studies conducted for the Assignee hereof have shown that the buffer composition employed has minimal effect on the virus particle in terms of viral inactivation and viral envelope removal.

SUMMARY OF THE INVENTION

The methods of the instant invention result in substantially pure immunoglobulin. The immunoglobulin may be a monoclonal or polyclonal immunoglobulin, for example monoclonal or polyclonal anti-D immunoglobulin, more particularly, RHOGAM® Rho(D) Immune Globulin (Human) or MICRHOGAM® Rho(D) Immune Globulin (Human).

The immunoglobulin formulation of the invention comprises from about 4.0% to 6.0% immunoglobulin by weight, from about 24 to 36 ppm Thimerosol, and from about 80 to 200 ppm polysorbate 80. More particularly, the immunoglobulin formulation of the invention comprises about 5.0% immunoglobulin by weight, about 33 ppm Thimerosol and about 100 ppm polysorbate 80.

The invention contemplates a method for making a substantially pure formulation of a large globular protein comprising the steps of (a) fractionating human plasma in alcohol; (b) resuspending the resulting Precipitate II; (c) admixing the resuspended Precipitate II with a high ionic strength buffer containing an excipient; and (d) performing nanofiltration on the immunoglobulin. The alcohol may be methanol. The high ionic strength buffer can be 150 mM NaCl-Glycine. The excipient is a non-ionic polyoxyethylene detergent, for example polysorbate-80.

The nanofiltration comprises use of a first nanofilter having a cutoff rating of less than about 30 nm, preferably about 12 nm. The filtration can further comprise use of a second nanofilter having a cutoff rating of about 10,000K to about 60,000K, preferably about 50,000K, which removes the methanol, concentrates the protein, and exchanges the buffer to that which is best for product stability. Such a buffer is for example a low ionic strength buffer, for example 50 mM NaCl Glycine buffer.

Also contemplated is a process for the manufacture of substantially pure anti-D antigen comprising the steps of:

(a) resuspending Precipitate II from fractionated human plasma;

(b) admixing the resuspended Precipitate II with processing aids; and (c) performing nanofiltration on the immunoglobulin. The processing aids comprise a high ionic strength buffer and a non-ionic excipient; the high ionic strength buffer comprises 150 mM NaCl Glycine buffer and the non-ionic excipient comprises polysorbate 80.

The methods of the invention may also include a step (d) concentrating the immunoglobulin concentration using a nanofilter having a cutoff rating of about 50,000K. This step also exchanges the high ionic strength buffer for low ionic strength buffer, for example 50 mM NaCl Glycine buffer.

BRIEF DESCRIPTION OF THE DRAWINGS

FIGS. 2A, 2B and 2C designate the Product Holding Tank as 1, the Viral Clearance Filter Holder as 2, the Ultrafiltration Filter Holder as 3, the 50 mM NaCl-Glycine Buffer Storage Tank as 4, the T-1 Recirculation Tank as 5, the T-2 UF Recirculation Tank as 6, the P1 Viresolve 180 Feed Pump as 7, the Viresolve 180 Permeate Pumpas 8, the UV Meter I as 9, the UF Feed Pump as 10, the UF Permeate as 11, the Sample Port as 12, and the Product Recovery and In-Line Sterile Filtration as 13.

DETAILED DESCRIPTION OF THE INVENTION

Figure 1:
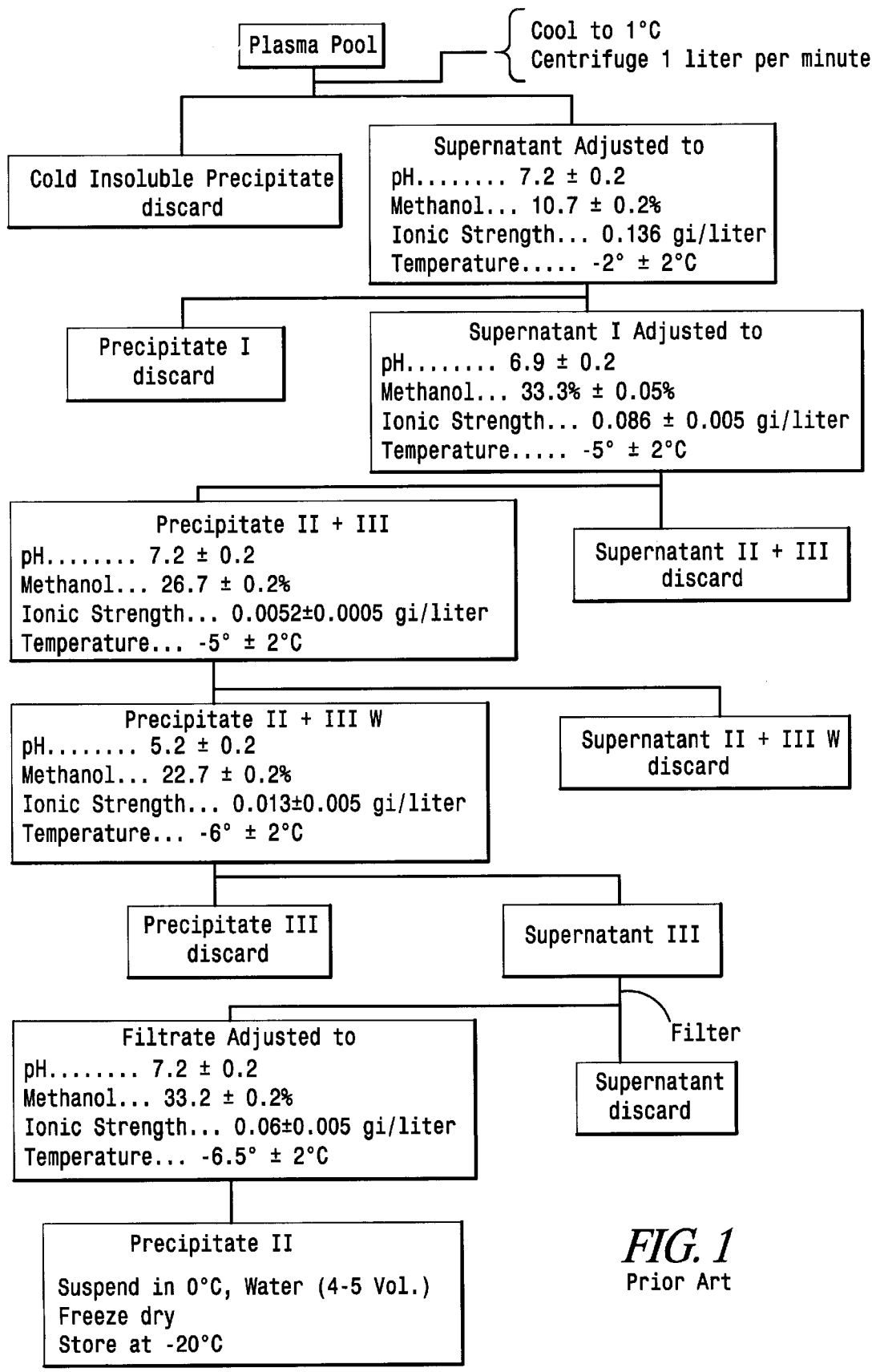
FIG. 1 is a flow sheet showing the process of fractionation of human plasma to obtain anti-Rh globulin.

The instant invention uses a combination of high (around about physiological range) ionic strength buffer and a non-ionic excipient as processing aids during viral reduction or viral clearance of a large biomolecule. This invention allows a small pore size exclusion nanofilter to be used with a globular protein molecule such as an immunoglobulin without appreciable yield loss and no significant change in immunoglobulin subclass, aggregate level or stability. The high ionic strength buffer and excipient are used only as processing aids and can be reduced by nanofiltration after processing. The methods of the invention yield a product substantially free of virus. Virus removed by the methods of the invention (size exclusion) ensures all potential categories of virus, both enveloped (for example, HIV, Hepatitis B Virus) and non-enveloped (for example, Hepatitis A Virus, Parvovirus B19), are removed from the product.

The advantages of the processing aids of the invention include (1) processing time is greatly reduced and concomitantly yield is greater, since the processing aids shift the equilibrium away from protein dimer, trimer and aggregate formation, which allows the product to be processed at an increased protein concentration, (2) the ability to use smaller pore size membrane allowing for greater assurance of viral clearance of the smaller non-enveloped virus, (3) the immunoglobulin processed through the membrane is not altered in IgG subclass or stability, and (4) processing equipment and therefore manufacturing floor space can be optimized for highest product yield per filter area.

The large molecules processed in accordance with the methods of the invention include large globular proteins such as albumin, immunoglobulins (for example IgG) and fragments thereof, blood coagulation factors such as Factors VIII, IX and XI, growth hormones, apolipoproteins, enzymes (for example streptokinase), all of the above whether naturally occurring or genetically engineered.

The pore size of the nanofiltering units employed in the production of substantially pure, virus-free immunoglobulin products of the instant invention is less than about 30 nm, most preferably less than about 15 nm. However, any membrane having the filter cutoff rating sufficient to reduce or eliminate non-enveloped virus from a proteinaceous solution can be employed in the processing methods of the invention. For example, the VIRESOLVE® 180 SYSTEM Ultrafiltration System (Millipore Corporation, Bedford, Mass.) unit may be employed, such unit having a molecular weight pore size rating of less than about 180 KD molecular weight or about 12 nm. The methods of the invention also contemplate the use of the 70 KD nanofilter pore size units currently used in the filtration of small recombinant proteins, cytokine and lymphokine products as well as blood fractionation products.

The instant use of a non-ionic excipient as a nanofiltering processing aid is novel. The non-ionic excipients of the instant invention include vinyl polymers, PLURONICS™ Polyoxyethylene-Polypropylene Polymers or Co-Polymers, polysaccharides, proteins, poly(ethyleneoxide), and acrylamide polymers and derivatives or salts thereof. It is understood that poly(ethyleneoxide) includes polyethylene glycol. The vinyl polymers useful in the present invention may be selected from the group consisting of polyacrylic acid, polymethacrylic acid, polyvinyl pyrrolidone and polyvinyl alcohol. The polysaccharides useful in the present invention may be selected from the group consisting of cellulose or cellulose derivatives, glycosaminoglycans, agar, pectin, alginic acid, dextran, starch and chitosan. The glycosaminoglycans may be selected from the group consisting of hyaluronic acid, chondroitin, and related molecules. The proteins useful in the present invention may be selected from the group consisting of gelatin and fibronectin. Although some of the materials listed hereinabove may not pass through a nanofilter, their presence on the retentate side thereof may be sufficient to accomplish the purposes of the invention.

The cellulose derivatives may include alkyl cellulose and hydroxyalkyl cellulose, for example, methyl cellulose, hydroxyethyl cellulose, carboxymethyl cellulose, hydroxypropylmethyl cellulose and hydroxypropyl cellulose.

Most preferred for the nanofiltration of globular proteins as contemplated in the instant invention are ionic detergents, nonionic detergents with polyoxyethylene or sugar head groups, lysopholipids, and bile salts and combinations thereof. Especially preferred are the nonionic polyoxyethylene detergents for example the polysorbates, PLURONICS™ Polyoxyethylene-Polypropylene Polymers or Co-Polymers, Brij, Sterox-AJ, Tritons and Tweens. Most preferred is polysorbate 80.

The non-ionic excipient of the instant invention may be present in the protein solution initially in the processing method in the range of from about 0.015 g/L to about 0.024 g/L, most preferably about 0.02 g/L or 20 ppm. Such concentrations of excipient during processing were determined not to affect viral clearance. Particularly preferred of the non-ionic excipients is polysorbate 80, which is employed most preferably during processing at a concentration of 0.002% or 20 ppm for processing. This range is at or within the critical micelle concentration for polysorbate 80. In determining concentrations for other excipients in this invention, guidance may be taken in the knowledge of the critical micelle concentration for that excipient. The amounts of excipient recited in this paragraph are specific for anti-D immunoglobulin, however, it is contemplated that said amounts would be applicable to other formulations of IgG, for example immune serum globulin (human and equine) and hepatitis B immune globulin. The final excipient concentration in product may be up to about 0.1–0.2% w/v; more preferably about 80–200 ppm, most preferably, in the case of polysorbate 80, about 100 ppm. In general, the amounts of excipient present in final product would be about the same for all IgG molecules that are administered in about the same dosage. A further advantage to the use of the excipient is as a de-foaming aid during the filtration processing.

The human plasma used in the instant invention can be obtained by the methods of Cohn et al. (the "Cohn process"), referenced hereinabove, by batch or column exchange chromatography, or by affinity chromatography.

In the process of the invention wherein the Precipitate II (from the Cohn et al. process) material is diluted to about 4.6–5.0 mg/ml (about 0.5%) and must be later concentrated 10× through ultrafiltration, it is important to use a low initial concentration of excipient; excipient concentration in the range stated hereinabove and preferably about 0.002% does not adversely affect the process. Such adverse effect could be for example with enveloped virus, the dissociation of the virus from its envelope and the passage of virus particles into the filtrate. Studies conducted for the Assignee hereof using Vesicular Stomatitis Virus, a bullet-shaped, enveloped, RNA-containing virus showed that at the concentrations of excipient employed in this invention (100 ppm or 0.01% at 5× for processing), no appreciable virus activation occurred.

The protein concentration used in the processing of the instant invention will be in the range of about 0.1% to about 1% by weight. Up to about 1% can be used where the protein material is monomeric or monoclonal. For the Precipitate II immunoglobulin used in the instant invention, the initial protein concentration used for processing is about 4.6–5.0 mg/ml (about 0.46–0.5%).

Cohn, U.S. Pat. No. 2,390,074, the contents of which are herein incorporated by reference, discloses a method of fractionating blood by which gamma globulins are prepared. The gamma globulins prepared by the Cohn method contain 19 S globulin, plasminogen and lipids. While this gamma globulin is eminently suitable for prophylaxis against diseases such as measles and tetanus, the presence of the 19 S globulin, plasminogen and lipids are unnecessary contaminants and may decrease its effectiveness in preventing immunization to the Rh-factor on the fetal erythrocytes.

The substantially pure anti-Rh globulin manufactured by the validatable processes of the present invention is prepared from human plasma which contains albumin, plasminogen, alpha, beta and gamma globulins and various lipids. Specifically, the anti-Rh globulin of the invention is a gamma globulin.

The fractionation of human plasma to obtain anti-Rh globulin is carried out according to the methods of commonly-assigned U.S. Pat. No. 3,449,314 to Pollack et al., the teachings of which patent are hereby incorporated by reference herein. With reference to the accompanying flow sheet of FIG. 1, the ability to fractionate human plasma is dependent upon the solubility of the various components of the plasma. At each stage of the fractionation, the separation of the fraction and the ultimate removal of those components which are undesirable in the anti-Rh globulin are determined by the critical control of pH, temperature, concentration of the precipitant and the ionic strength of the system.

Various organic solvents of low dielectric constant such as acetone and alcohols, precipitate proteins and have been used in the fractionation of plasma. The organic solvents utilized in the method of this invention include the various alcohols and acetone, preferably methanol. Methanol is preferable due to its comparatively lower toxicity and safer handling (e.g., explosion danger) that other organic solvents.

In order to prevent denaturation of the proteins during fractionation, precipitation is carried out at low temperatures. Since protein solubility is temperature dependent, the temperature chosen for each step of the fractionation must be the lowest possible which permits the desired separation in order to prevent denaturation.

Referring to the flowsheet of FIG. 1, the fractionation proceeds from whole human plasma. The plasma is cooled to about 1° C. and is then centrifuged to separate a cold insoluble precipitate from a supernatant. The supernatant is further fractionated to yield Precipitate I and Supernatant I. Precipitate I which consists principally of fibrinogen is discarded. Supernatant I is further fractionated to yield Supernatant II+III and Precipitate II+III. Supernatant II+III, which is discarded, contains alpha and beta globulin and lipids. Precipitate II+III consists principally of beta and gamma globulins and isoagglutinins, but also contains prothrombin, plasminogen, cholesterol and other lipids. Precipitate II+III, upon further fractionation yields Supernatant II+III W and Precipitate II+IIIW. The beta globulin, cholesterol and other lipids are largely removed in Supernatant II+III W which is discarded. Precipitate II+III W consists principally of gamma globulins, isoagglutinins, plasminogen and prothrombin and some beta globulin, cholesterol and other lipids. Upon further fractionation, Precipitate II+III W yields Supernatant III+Precipitate III. Precipitate III, which is discarded, contains isoagglutinins, plasminogen and prothrombin. Supernatant III consists principally of gamma globulins and minor amounts of fibrinogen and lipids. The final step of the fractionation yields Precipitate II which is essentially pure gamma G globulin almost completely free of 19S globulin, plasminogen and lipids. Precipitate II prepared by the process of the invention is an anti-Rh gamma globulin.

In the preferred methods of the invention, the immunoglobulin starting material for resuspension is the Precipitate II paste from the modified Cohn process. Lyophilized precipitate II paste may be used if the protein is lyophilized in the presence of excipient such as those contemplated by the instant invention.

The liquid diluent employed to resuspend the Precipitate II paste in the invention include the pharmaceutically acceptable diluents chosen from Water for Injection, U.S.P. ("W.F.I."), normal saline U.S.P., or any of a range of suitable buffers, the latter of which provides the advantage of providing for a stable pH. Suitable buffers are those selected from the group consisting of phosphate buffers, citrate buffers, borate buffers, acetate buffers and glycine buffers at a pH of about 6.4. Preferably the initial diluent is 3× paste by weight of W.F.I. which is later diluted in high ionic strength buffer prior to the first nanofiltration. Also suitable as the initial diluent is the high ionic strength buffer contemplated herein. Preferably an ionic strength of 150 mM+/−20% is employed, preferably 150 mM+/−20% NaCl Glycine buffer; pH 6.4.

During processing and filtration of the immunoglobulins of the invention, a high ionic strength buffer is preferably used as a processing aid to decrease the dimer and trimer formation of the immunoglobulin, allowing more complete passage through the filter. The suitable high ionic strength diluents are those recited hereinabove for resuspension diluents, however, at a relatively higher ionic strength and a pH of about 6.4. Preferably such processing aids are present at an ionic strength of about 150 mM+/−20% concentration being most preferable, which is about physiological ionic strength. In the most preferred embodiment of the invention, the high ionic strength processing aid is 150 mM NaCl-Glycine buffer, pH 6.4.

In the processing of the immunoglobulins of the invention, the non-ionic excipient can conveniently be admixed with the high ionic strength buffer at the commencement of the filtration step of the process. Reference is made in this regard to Examples 2A and 3A for preparation of the high ionic strength buffer containing polysorbate 80. The processing aids of the invention can be adjusted relative to each other such that ionic strength content can be reduced if polysorbate 80 concentration is increased.

Preservatives may be used in the pharmaceutical products resulting from the processing methods of this invention. Preferred preservatives are those pharmaceutically-acceptable preservatives such as thimerosol and sodium azide, the former which may be used at 26–36 ppm, in this invention, 33 ppm (0.003%). However, in the immunoglobulin formulations of the invention and particularly the RHOGAM® Rho(D) Immune Globulin (Human) and MICRHOGAM® Rho(D) Immune Globulin (Human) formulations which are designed as single use parenterals, it is not necessary to employ preservatives.

In the protein concentration and organic solvent removal step of the invention for example using a second small pore size nanofiltration filter, for example, a filter from about 10,000K up to about 60,000K cutoff, for example BIOMAX™ 50 Filter (Millipore Corporation, Bedford, Mass.) having a 50,000 dalton cutoff filter, the high ionic strength buffer may optionally be exchanged for relatively low ionic strength, for example 50 mM buffer. This protein concentration step serves to concentrate the nanofiltered protein product while removing some of the excipient and the organic solvent.

During filtration using the VIRESOLVE®,180 SYSTEM Ultrafiltration System, the transmembrane pressure is preferably in the range of about >0 to about 3.0 psi, most preferably less than about 1.5 psi. The sieving coefficient will preferably be greater than about 60%.

The processing of the instant invention can be carried out at ambient temperatures. Processing at refrigerated temperatures will generally prolong the filtration time as such temperatures (e.g., 16–17 C.) will generally increase the viscosity. The temperature of the product during processing can be from about 0 C. or just above to about 45 C., more preferably from about 15 C.–30 C., most preferably about 20 C.–25 C.

Figures 2, 2A:
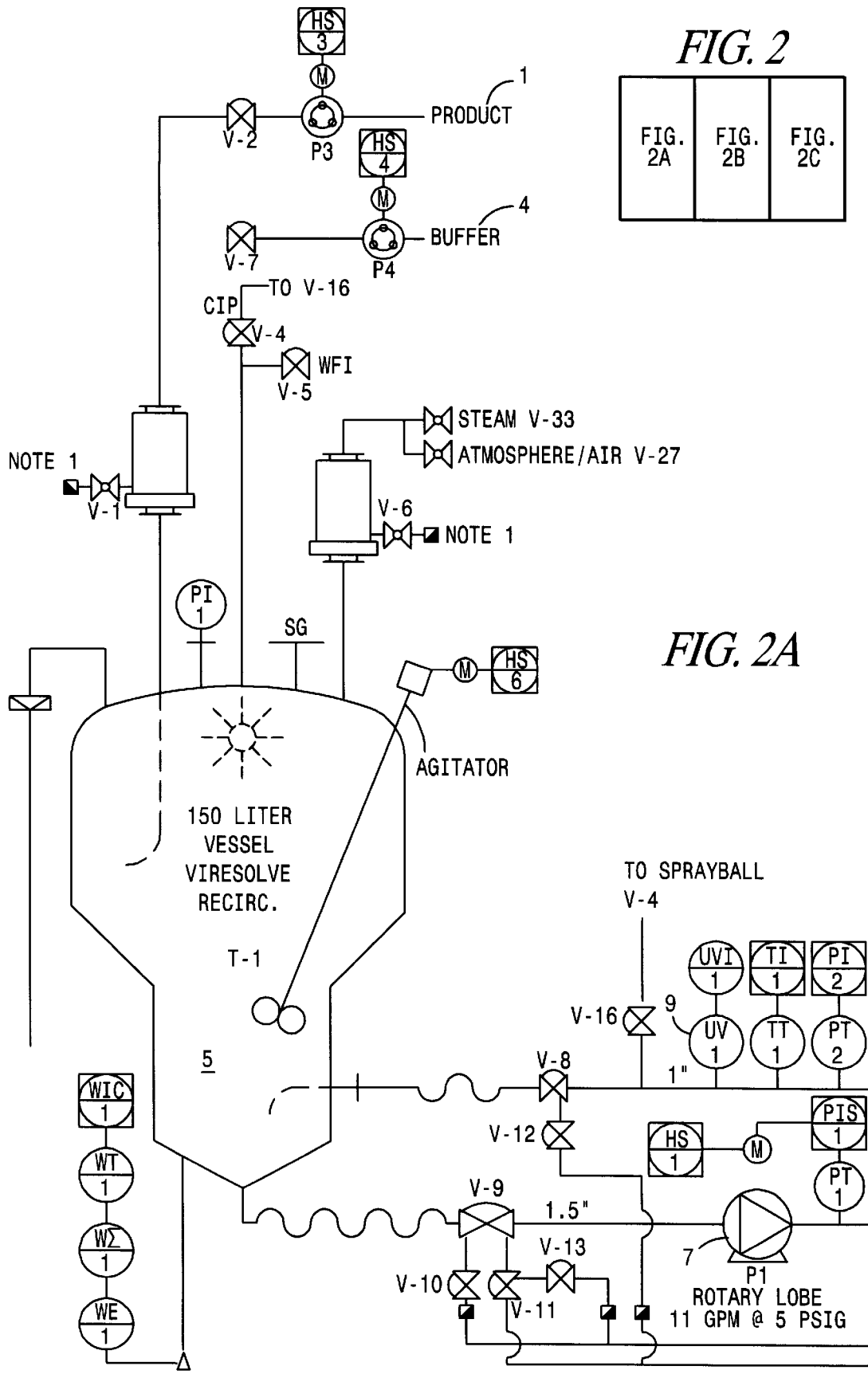
FIGS. 2A, 2B and 2C are schematic drawings showing the VIRESOLVE® 180 SYSTEM Ultrafiltration System used in the viral clearance process of the invention.
Figure 2B:
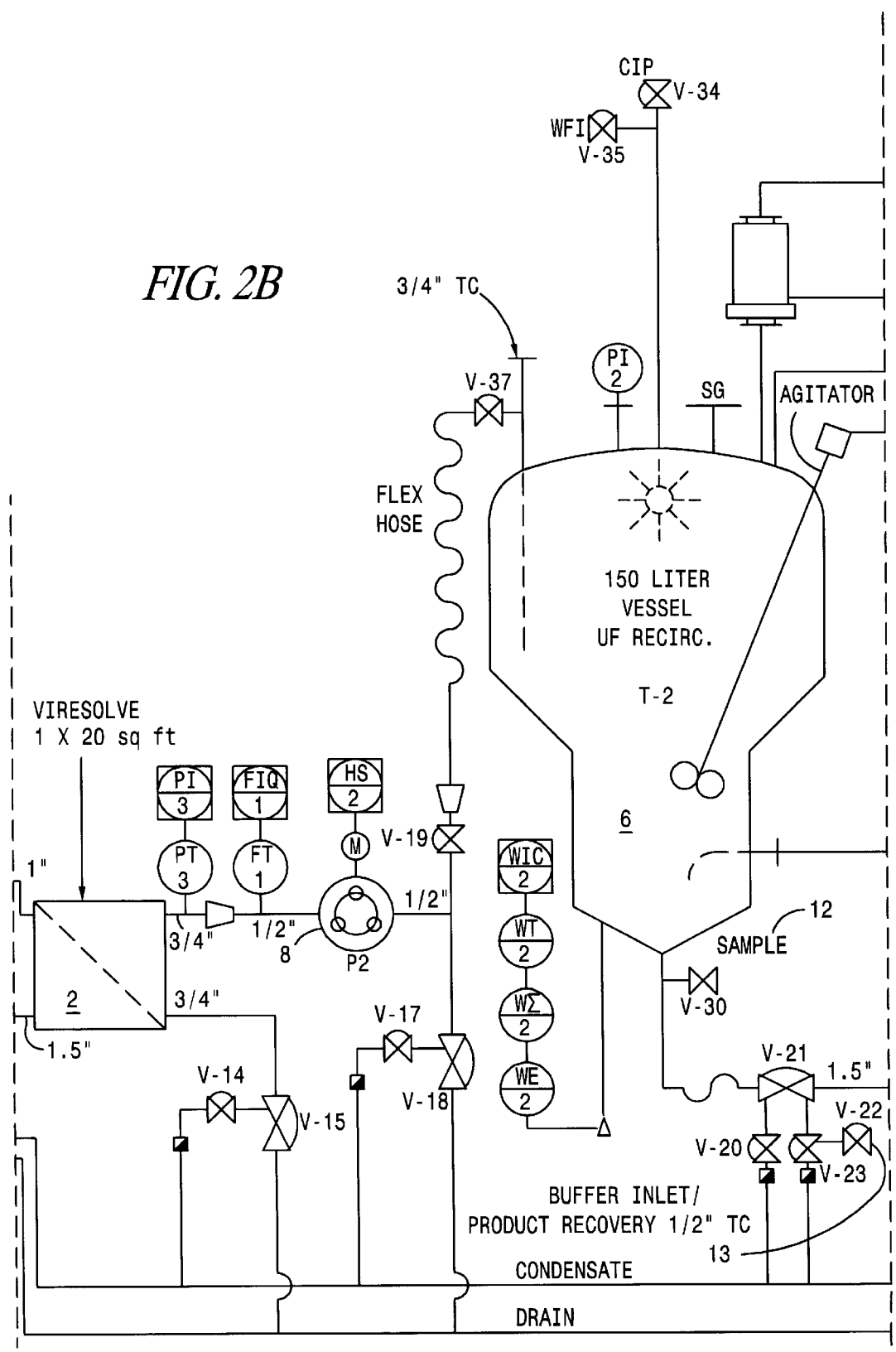
Figure 2C:
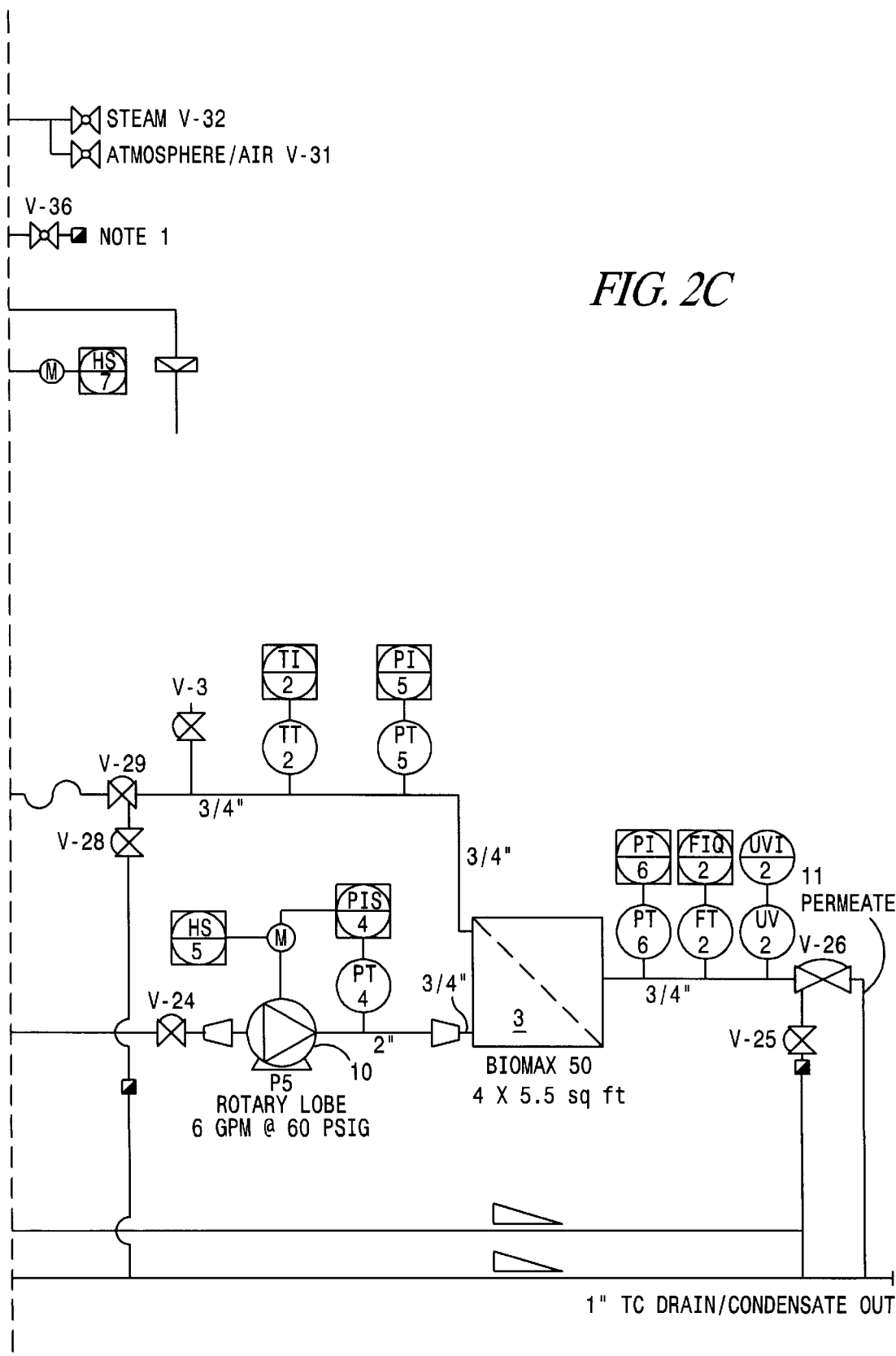

The following terms as used herein have the meanings ascribed to them as follows:

Cross Flow Rate: Flow rate in mL/min of the feed solution across the membrane surface
Permeate: Purified product which passes through the membrane
Retentate: Material retained by the membrane
Flux: Permeate Flow Rate/Area
Conversion: Permeate Flow Rate/Cross Flow Rate
Sieving Coefficient: Protein Content of Permeate/Protein Content of Retentate In one embodiment of the instant invention, and with reference to FIGS. 2A, 2B and 2C, manufacture scale processing to result in substantially pure (virally-cleared) immunoglobulin, for example, RHOGAM® Rho(D) Immune Globulin (Human), by nanofiltration proceeds as follows:

Rho(D) Immune Globulin is purified to step "Precipitate II paste" using the Cohn purification method (Cohn et al., J. Am. Chem. Soc., Vol. 68, pages 459–475), in which methanol is substituted for ethanol, resuspended in Water for Injection (WFI), U.S.P. cooled to from 2–8 C. The volume of W.F.I. is calculated using the following formula:

Precipitate II wt. (kg)×3 L/kg=Req. Vol. of W.F.I. (L)

Each kg of Precipitate II paste is resuspended in 3 L of W.F.I.

The admixture is vortexed (no foaming) for 3–8 hours in Hold Tank—Product (1) and stored at 4 C. until further use. Steam in place (SIP) procedure is performed on the viral clearance system, which includes installation of a VIRESOLVE® 180 SYSTEM Ultrafiltration System CIP/SIP module (Millipore Corporation, Bedford, Mass.) into the viral clearance filter holder (2) and a PELLICON® SYSTEM Filtration System CIP/SIP module (Millipore Corporation, Bedford, Mass.) onto the ultrafiltration filter holder (3). The CIP/SIP procedure is also performed on the system and the 50 mM NaCl—Glycine Buffer storage tank (4).

The Clean in Place (CIP) procedure is a method of cleaning processing equipment without disassembly of the equipment parts. Requirements in the equipment include that all piping is stainless steel, are in proper pitch and alignment and have a minimum number of gaskets. Objectives of the CIP are to eliminate manual cleaning and cross contamination of lots. The procedure can be validated. Elements of cleaning include time, temperature, chemical and mechanical parameters. The type of residue remaining post processing will determine the cleaner that is to be used in the CIP procedure. A person having ordinary skill in the pharmaceutical processing art is familiar with the process and requirements of CIP.

Following the SIP procedure, a VIRESOLVE® 180 SYSTEM Ultrafiltration System module, 20 stack (2) for the approximately 40 L volume of resuspended Precipitate II volume is installed in place of the VIRESOLVE® 180 SYSTEM Ultrafiltration System CIP/SIP module (2). (A 10 stack VIRESOLVE® 180 SYSTEM Ultrafiltration System filter is used for 10–16 L, and a 20 stack for >16–40 L final product volume.) Four BIOMAX™ 50 Filter cassettes (Millipore Corporation, Bedford, Mass.) are installed in place of the PELLICON® SYSTEM Filtration System CIP/SIP module (3). Two BIOMAX™ 50 Filter cassettes are used with 10–16 L of resuspended Precipitate II volume, four cassettes are used for >16–40 L of volume. The VIRESOLVE® 180 SYSTEM Ultrafiltration System module is sanitized with chlorine and rinsed until chlorine is determined present d 0.3 ppm chlorine by the diethylphenylene diamine (DPD) procedure.

A pressure hold test is performed on the module (2) post-sanitation. The module must withstand a minimum of 10 psi and demonstrate a pressure drop of d 1 psi over the required 5 minute testing period.

The BIOMAX™ 50 Filter membranes (3) are flushed with WFI, U.S.P. Determination of Benzalkonium Chloride (Roccal) is performed on a final permeated flush sample; the benzalkonium chloride content must be $\leq 10$ ppm. A diffusion test is performed on the Biomax-50 cassettes; release rate is calculated as follows:

$$\frac{\text{Volume Released (cc)}}{} \div \frac{\text{Time Period (min)}}{} \div \frac{\text{Number Cassettes}}{} = \frac{\text{Release Rate (cc/min/cassette)}}{}$$

The release rate must be $\leq 18$ cc/min/cassette.

A viral clearance ultrafiltration using a VIRESOLVE® 180 SYSTEM Ultrafiltration System (2) is performed on the 50 mM NaCl Glycine buffer. The viral clearance recirculation tank (T-1) (5) is charged with 50 mM NaCl-Glycine buffer. A maximum of 250 L is charged with a minimum of 130 L.

The buffer is recirculated in T-1 (5) while collecting the buffer permeate in a tank off-line.

The viral clearance recirculation tank (T-1) (5) is charged with a minimum of 60 L of the 150 mM NaCl-Glycine buffer to flush the tank and membrane.

The Precipitate II resuspension is processed as follows. Precipitate II is mixed at a rate which creates a vortex without foaming, for 15–30 minutes until completely suspended. Percent Protein by Refractive Index (mg/ml protein) is performed using hand held protometer on the Precipitate II resuspension. The required final volume of diluted Precipitate II to achieve 5.0 mg/ml protein concentration is calculated using the following formula:

$$\frac{\text{Resuspended Ppt. II Vol. (L)} \times \text{Actual Protein Conc. (mg/ml)}}{5.0 \text{ mg/ml}} = \frac{\text{Req. Dil. Ppt}}{\text{II Vol. (L)}}$$

The required volume of 150 mM NaCl Glycine buffer is calculated using the following formula:

$$\text{Reg. Dil. Ppt. II Vol. (L)} - \text{Resuspended Ppt. II Vol.(L)} = \text{Vol. buffer to add (L)}$$

Buffer is added to diluted Precipitate II and mixed at a speed sufficient to create a vortex without foaming for a minimum of 30 minutes. The admixture is stored at 15–30 C. a maximum of 2.5 hours until further processing.

The batch of diluted Precipitate II is charged into the viral clearance recirculation tank (T-1) (5) for ultrafiltration. The TMP setpoint is set at about 3.0. However, it may go higher however if it reaches about 12 the membrane may be polarized and the retentate should be permitted to wash the membrane (by reducing the permeate). The VIRESOLVE® 180 SYSTEM Ultrafiltration System level setpoint is calculated as follows:

$$\frac{\text{Total Vol. of Diluted PPT II (L)}}{3} = \frac{1}{3} \text{Total Vol. (L)}$$

If the above result is <50, 50 was entered as the VIRESOLVE® 180 SYSTEM Ultrafiltration System level setpoint setting. The ⅓ total volume is rounded to the nearest whole L.

The Ultrafiltration concentration endpoint is calculated as follows:

$$\frac{\text{Total Vol. Diluted PPT II (L)}}{12} = \text{Conc. endpoint}$$

If the above result is <20, 20 was entered as the conc. endpoint. The ultrafiltration diafiltration endpoint is calculated as follows:

$$\text{Conc. endpoint} - 3 = \text{Diaf Endpoint}$$

The diafilter total setpoint is calculated as follows:

$$\text{Conc Endpoint} \times 5.5 = \text{Diafilter total Setpoint (L)}$$

To begin the ultrafiltration/concentration process, the VIRESOLVE® 180 SYSTEM Ultrafiltration System feed pump (P1) (7) rate is ramped to 75%–83% for the 20 stack, or 37%–42% for the 10 stack filter size. The TMP control is engaged; the TMP is controlled by the rate of the permeate pump (P2); if the transmembrane pressure goes to 3.0 then the pump will slow down. The VIRESOLVE® 180 SYSTEM Ultrafiltration System permeate pump (P2) (8) rate is ramped slowly up to 18%, or 9% for the 10 stack filters. Once P2 is ramped up, a retentate pressure (PT3) of $\geq 5.0$ psi is maintained. Once the TMP equilibrates, the pump rate range is set to 9%–11% for the 10 stack filter; 18%–23% for the 20 stack filter. The TMP pressure is not controlled; however, it is preferably relatively low, e.g., at about less than 3.0 psi, or the membrane may become polarized. Should the TMP become higher, for example around 12 psi, the permeate may be stopped so the retentate can wash the membrane. The UV meter (UV1) (9) should be between the lower limit of 4.0 A.U. and the upper limit of 7.7 A.U. The permeate flow (FT1) is between the lower limit of 0.81 liter/min (LPM) and the upper limit of 0.98 LPM; between 0.40 LPM-0.49 LPM for a 10 stack filter. The processing temperature is maintained at about 15–30 C. These conditions are monitored throughout the viral clearance/ultrafiltration process. The UV meter (UV1) (9) is between the lower limit of 6.4 A.U. and the upper limit of 7.7 A.U. Sieving coefficient should be about $\geq 75\%$.

When the T-2 (6) volume reaches approximately 75–100 L, the PELLICON® SYSTEM Filtration System (3) is set up and begun mixing. The UF feed pump (P5) (10) is started/ramped up, and the UF permeate flowrate controlled by the pump rate. The UF feed pressure (PT4) and UF retentate pressure (PT5) is maintained as follows:

UF Feed Pressure: $\leq 30$ psi

UF Retentate Pressure: $\leq 10$ psi

A differential is maintained between feed pressure and retentate pressure of $\leq 20$ psi Feed pressure (psi)–retentate pressure (psi)=differential (psi)

The volume levels in the diluted Precipitate II feed tank T-1 (5) is monitored (by weight) and responded to by load cells on T-1.

Constant volume diafiltration is performed in T-1 (5). This diafiltration is used to wash the residual protein through the system and the VIRESOLVE® 180 SYSTEM Ultrafiltration System membrane thereby increasing the yield. A 3×150 mM NaCl-Glycine buffer diafiltration is performed; a set amount of buffer is added at the same rate that it is being removed through the VIRESOLVE® 180 SYSTEM Ultrafiltration System permeate. Once the diafiltration steps are completed, T-1 (5) and the VIRESOLVE® 180 SYSTEM Ultrafiltration System module (2) are sanitized as described hereinabove, using the chlorine process, insuring that any virus held up will be inactivated. The bulk in T-2 (6) is concentrated by constant volume diafiltration in T-2 (6), with the virally-cleared 50 mM NaCl-Glycine buffer. This step concentrates the bulk product and exchanges the higher ionic strength buffer concentration for a lower ionic strength concentration, removes the methanol from the Cohn process, and about half the polysorbate 80. After the diafiltration process is completed, the level in T-2 (6) is recorded in liters. A sample is drawn from T-2 (6) to perform a digital specific conductance determination on the UF permeate sample. The result must fall between $4.95-5.67 \times 10^{-3}$ mhos/cm. If the requirement is not met on the first test, constant volume diafiltration must be continued until the test result is within this required range.

T-2 level after the 5.5× diafiltration should be $\leq 95\%$ of the resuspended Precipitate II volume. If T-2 level is >95% of the resuspended Precipitate II volume, continue to concentrate the bulk until the T-2 volume meets the upper volume level requirement. Once the volume level is met, the UF permeate is shut off (11) and the bulk mixed by recirculation, and a 10.5 ml sample aseptically removed (12). Percent protein determination is made by refractive index using the hand held protometer on a 0.5 ml aliquot of the sample. If the protein concentration is not at least about 5.5%, the sample must be further concentrated until such minimum percent is met. The bulk is moved to an interim vessel and the bulk weight is calculated gravimetrically using the following formula:

$$\text{Filled Interim Vessel Weight (kg)} - \text{Interim Vessel Tare Weight (kg)} = \text{Bulk Product weight in } T-2 \text{ (kg)}$$

Bulk adjustments can be made by determining the volume of 50 mM NaCl-Glycine buffer to add to achieve final bulk volume by using the following formula:

$$\frac{\text{Actual \% Protein} \times \text{Bulk Volume (L)}}{\text{Desired \% Protein (5.0\%)}} = \text{Required Final Volume (L)}$$

The required volume of 50 mM NaCl-Glycine buffer to add is calculated as follows:

$$\text{Required Final Volume (L)} - \text{Bulk Product Volume in } T-2 \text{ (L)} = \text{Required Volume of 50 mM NaCl} - \text{Glycine}$$

An initial pH determination is made on the remaining sample aliquot, by first diluting the aliquot 1:10 with 0.9% NaCl and titrated to a pH of 6.3–6.4 with 1:100 dilution of 0.5N HCl or 0.5N NaOH.

If adjustment is required, the amount of undiluted 0.5N reagent required to adjust the pH of the bulk is calculated as follows:

$$\text{Required Final Volume (L)} - \text{Volume of 1:100 titrant required (ml)} = \text{Volume of undiluted 0.5N reagent (ml)}$$

Integrity testing is performed on the Viresolve-180 filter module in accordance with accepted methods. The integrity test value must be $\geq 0.2$, and the module must be sanitized with chlorine as above and rinsed.

0.5N undiluted reagent calculated using the formula hereinabove and, if desired, 100× thimerosol solution are added to the bulk. The required amount of thimerosol solution to add, if desired, is calculated as follows:

$$\frac{\text{Required Final Bulk Volume (L)}}{100} = \text{Required Volume of 100× Thimerosol Solution (L)}$$

50 mM NaCl-Glycine buffer is added to the bulk as calculated by the following formula:

$$\text{Tank 2 Level (L)} + \text{50mM NaCl} - \text{Glycine} = \begin{array}{l} \text{Required Volume of Tank 2 Level for} \\ \text{Required Final} \\ \text{Buffer (L)} \\ \text{Volume of Bulk} \end{array}$$

The bulk is pumped back into T-2 and continued to mix in T-2 for 10–60 minutes after required final volume was reached, then 10.5 ml aliquot of bulk product is aseptically removed for determination of pH. pH must be 6.3–6.4. If pH is outside of the stated range, an aliquot must be diluted and titrated to the acceptable pH as before and the required amount of undiluted 0.5N reagent must be calculated and added back into the bulk while mixing, as hereinabove.

The percent protein is determined by refractive index using the hand-held protometer as above. If the protein concentration is $\geq 5.0\%$, which is acceptable, the bulk may pass through to the next step. If the protein concentration is less than the acceptable percentage, the bulk product is rejected.

The bulk is optionally filtered through a 0.2 u Optiseal filter (13), with the pressure not exceeding 15 psi during the filtration process, then the bulk is microbiologically and serologically tested.

A clean-in-place procedure, consisting of rinsing with WFI and steam, is performed on the viral clearance system (CIP procedure described hereinabove).

Acceptance criteria for the product are listed in Table 1.

TABLE 1

| Characteristic | Requirement |
|---|---|
| Protein | 4.0 to 6.0% |
| pH | 6.3 to 6.4 |
| Thimerosol | 24 to 36 ppm |
| Polysorbate 80 | 80 to 200 ppm |
| Methanol Content | <50 ppm |

The mode of administration of the preparations of the invention may determine the sites and/or cells in the organism to which the compound(s) will be delivered. The compounds of the invention can be administered alone but will generally be administered in admixture with a pharmaceutical carrier or diluent selected with regard to the intended route of administration and standard pharmaceutical practice. The preparations may be injected parenterally, for example, intra-arterially or intravenously. The preparations may also be delivered via oral, subcutaneous, or intramuscular routes. For parenteral administration, they can be used, for example, in the form of a sterile, aqueous solution which may contain other solutes, for example, enough salts or glucose to make the solution isotonic.

For the oral mode of administration, the EPO compositions of the invention can be used in the form of tablets, capsules, lozenges, powders, syrups, elixirs, aqueous solutions and suspensions and the like. In the case of tablets, carriers which can be used include lactose, sodium citrate, and salts of phosphoric acid. Various disintegrants such as starch, and lubricating agents such as magnesium stearate are commonly used in tablets. For administration in capsule form, useful diluents are lactose and high molecular weight polyethylene glycols. When aqueous solutions are required for oral use, certain sweetening and/or flavoring agents can be added.

The substantially pure immunoglobulins of the present invention may be administered to a subject such as a mammal, including humans. For administration in the treatment of afflictions, the prescribing physician or veterinarian will ultimately determine the appropriate dose for a given human or animal subject, and this can be expected to vary according to the weight, age, and response of the individual as well as the nature and severity of the individual's symptoms.

In the case of the substantially pure anti-D immunoglobulin of the invention, the per-dose dosage will range from about 300 ug for RHOGAM® Rho(D) Immune Globulin (Human) and about 50 ug for MICRHOGAM® Rho(D) Immune Globulin (Human), each of which are administered in accordance with the guidelines and for the purposes discussed hereinabove and in the respective product literature. Each of the products mentioned above can also be multi-dosed, for a total delivery to be determined by the treating physician.

The following examples are provided for the purposes of illustration only and are not to be viewed as a limitation of the scope of the invention.

EXAMPLES

Example 1

Manufacture of virally-cleared RHOGAM® Rho(D) Immune Globulin Human by ultrafiltration proceeded as follows.

Rho(D) Immune Globulin 3.250 KG purified to step "Precipitate II paste" using the modified Cohn purification method (referenced hereinabove) was resuspended in 9.750 L of Water for Injection (WFI), U.S.P. cooled to 5 C. The admixture was vortexed (no foaming) for 4 hours, and stored at 4 C. until further use. The weight of the resuspended PPT II was 3.250 Kg.

Following the SIP procedure, a VIRESOLVE® 180 SYSTEM Ultrafiltration System module (Millipore Corporation) (10 stack) for the approximately 13.0 L volume of resuspended Precipitate II volume was installed. Two BIOMAX™ 50 Filter cassettes were installed in place of the PELLICON® SYSTEM Filtration System CIP/SIP module. The VIRESOLVE® 180 SYSTEM Ultrafiltration System module was sanitized with chlorine and rinsed. The BIOMAX™ 50 Filter membranes were flushed with WFI, U.S.P. Determination of Benzalkonium Chloride (Roccal) was performed on a final permeated flush sample; the benzalkonium chloride content was 6 ppm. A diffusion test was performed on the BIOMAX™ 50 Filter cassettes; release rate was calculated as described hereinabove; total volume released was 2 ml in 5 minutes, and the actual release rate was 0.4 cc/minute.

A viral clearance ultrafiltration using a VIRESOLVE® 180 SYSTEM Ultrafiltration System was performed on 190.0 L of the 50 mM NaCl Glycine buffer. The viral clearance recirculation tank (T1) was charged with 100 L of 50 mM NaCl—Glycine buffer. The buffer was recirculated in T1 while collecting the buffer permeate in the previously-sanitized 50 mM NaCl—Glycine buffer storage tank. Volume of permeated buffer collected was 123.3 L, at 21.7 C., and the collection was completed in 50 minutes. Virally cleared buffer was stored at ambient temperature of about 25 C.

A 150 mM NaCl-Glycine buffer (see Example 2A) flush was performed by attaching the buffer feed tank to the viral clearance recirculation tank (T1). T1 was charged with 60 L of the 150 mM NaCl-Glycine buffer to flush.

The Precipitate II resuspension was processed as follows. The Precipitate II (3250 g) was mixed at a speed creating a vortex without foaming, for 20 minutes, until completely suspended. Percent Protein by Refractive Index (mg/ml protein) was performed using hand held protometer on the Precipitate II resuspension, and was 49 mg/ml (about 5.0% protein).

The required volume of diluted precipitate II was calculated to achieve a protein concentration of 5.0 mg/ml:

$$\frac{\text{Actual Ppt. II Vol. (L)} \times \text{Actual Protein Conc. (mg/ml)}}{5.0 \text{ mg/ml}} = \text{Reg. Dil. Ppt. II Vol. (L)}$$

OR $$\frac{(13.0 \text{ L}) \times (49.0 \text{ mg/ml})}{5.0} = 127.4 \text{ L Dil. Ppt. II vol.}$$

The required volume of 150 mM NaCl Glycine buffer containing 20 ppm polysorbate 80 (see Example 1A) was calculated using the following formula:

$$\frac{\text{Reg. Dil. Ppt. II Vol. (L)} - \text{Vol. buffer to}}{\text{Resuspended Ppt. II Vol. (L)}} = \text{add (L)}$$

OR $$(127.4 \text{ L}) - (13.0 \text{ L}) = 114.4 \text{ L Buffer to add}$$

114.4 L of buffer was added to 13 L of diluted Precipitate II and mixed at a speed sufficient to create a vortex without foaming for 45 minutes.

The viral clearance recirculation tank was charged with 100.0 L of diluted Ppt.II. The viral clearance recirculation tank (Pump No. 1) was started at a feed pump rate of 40% for the 10 stack VIRESOLVE® 180 SYSTEM Ultrafiltration System module being used. The viral clearance permeate pump flow rate (Pump No. 2) was ramped to 0.450 LPM (10.0%) for the 10 stack module to maintain an initial transmembrane pressure (TMP) of <1.6 psi. The actual pressure maintained was 1.6 psi. The product pump rate (Pump No. 3) was adjusted to level control. The TMP was maintained at ≦3.0 psi throughout the process by monitoring the protein concentration on the retentate side of the viral clearance recirculation tank. The in-line UV monitor was observed and maintained at a range of 6.4–7.7 absorbance units to correspond to a protein content on 4.5–5.5 mg/ml.

After approximately 75 L of permeate from the viral clearance tank was charged into the ultrafiltration tank (UF), the ultrafiltration feed pump (Pump No. 5) was started at 10%. The pump speed was increased (to 30%) until the UF permeate flow rate equals the flow rate of the viral clearance permeate, then set at 25% to maintain the volume. The UF permeate flow rate was 0.4 LPM and the VC permeate flow rate was 0.460 LPM. The UF tank constant volume maintained was 75.3 L. The UF Feed pressure was 5.4 psi, the UF permeate pressure 0.2 psi and the UF retentate pressure 0.3 psi.

Constant volume diafiltration was performed in T1 once the tank contained about 15–20 L. Diafiltration was maintained with a minimum of three buffer exchanges of 150 mM NaCl Glycine buffer (about 60 L total volume). The viral clearance tank pumps and mixer were turned off when the diafiltration was completed. The VC recirculation tank constant volume was 16.2 L maintained. The total buffer volume exchanged was 49 L. The viral clearance diafiltration was completed in about 4 hours from the time the UF feed pump had been initiated.

The bulk in T2 was recirculated and thereby concentrated by constant volume diafiltration in T2, with the virally-cleared lot of 50 mM NaCl-Glycine buffer (containing no polysorbate 80). The bulk was thereby concentrated to about the original starting volume of resuspended Ppt II. The permeate valve was fully open, and the UF feed pump rate was 65%; the feed pressure was maintained below 30 psi and the pressure differential maintained at 14–17 psi by applying back pressure to the retentate loop. The UF constant column maintained was 20 L and the total buffer volume exchanged was 110 L. A sample was drawn from T2 to perform a digital specific conductance determination on the UF permeate sample. The result was $5.29 \times 10^{-3}$ mhos/cm. Once the volume level was met, the UF permeate was shut off and the bulk mixed by recirculation, and a 10.5 ml sample was aseptically removed. Percent protein determination was made by refractive index using the hand held protometer on a 0.5 ml aliquot of the sample. The protein concentration was 4.8%.

The required final volume of the bulk to achieve a 5% protein content was calculated as follows:

$$\frac{\text{Actual \% Protein} \times \text{Bulk Volume (L)}}{\text{Desired \% Protein (5.0\%)}} = \text{Required Final} \div \text{Vol (L)}$$

OR $$\frac{(4.8\%) \times (11.9 \text{ L})}{5.0\%} = 11.424 \text{ L Required Volume}$$

The bulk was further concentrated to meet the required 5% protein concentration to a final volume of 11.424.

An initial pH determination was made on the remaining sample aliquot, by first diluting the aliquot 1:10 with 0.9% NaCl and titrated to a pH of 6.3–6.4 with 1:100 dilution of 0.5N HCl or 0.5N NaOH. pH was 6.58.

To adjust the pH, 1.8 mL of titrant 0.5N HCl in 0.9% NaCl was added, and the final pH was 6.31. If adjustment is required, the amount of undiluted 0.5N reagent required to adjust the pH of the bulk is calculated as follows:

$$\frac{\text{Required Final}}{\text{Volume (L)}} - \frac{\text{Volume of 1:100}}{\text{titrant required (ml)}} = \frac{\text{Volume of undiluted}}{0.5\text{N reagent (ml)}}$$

OR, in this case:

11.424 L×1.8 ml=20.563 ml undiluted 0.5N reagent

Integrity testing was performed on the VIRESOLVE® 180 SYSTEM Ultrafiltration System filter module in accordance with accepted methods. The integrity test value must be e1.2, and the module must be sanitized with chlorine as above and rinsed.

The required volume of 100× Thimerosol Solution was calculated:

$$\frac{\text{Actual Conc. } 100 \times \text{Thimerosol ppm}}{1000} = \text{Actual Conc. } 100 \times \text{Thimerosol (g/L)}$$

OR $$\frac{3439}{1000} \text{ ppm} = 3.439 \text{ g/L actual conc. of } 100 \times \text{Thimerosol}$$

$$\frac{\text{Reg. Final vol. (L)} \times 0.03\text{g/L} \times 1000 \text{ ml/L}}{\text{Actual Conc. } 100 \times \text{Thimerosol g/L}} = \text{Reg. Volume } 100 \times \text{Thimerosol}$$

$$\frac{(11.424) \text{ L} \times 0.03 \text{ g/L} \times 1000 \text{ ml/L}}{3.439 \text{ g/L}} = 99.7 \text{ ml of } 100 \times \text{Thimerosol Required}$$

While constantly mixing the bulk, 99.7 ml of 100× Thimerosol was added.

The bulk was adjusted to the calculated required final volume with 0.70 L of virally-cleared 50 mM NaCl-Glycine Buffer and mixed for ten (10) minutes.

A 10.5 ml aliquot of bulk product was aseptically removed for determination of pH. pH must be 6.3–6.4. Actual pH was 6.54. Since pH was outside of the stated range, an aliquot was diluted and titrated to the acceptable pH as before and the required amount of undiluted 0.5N reagent must be calculated and added back into the bulk while mixing, as hereinabove.

$$\frac{11.9 \text{ L Required Final Volume (L)} \times 1.7 \text{ mL}}{1.7 \text{ mL Volume of } 1:100 \text{ titrant required}} = 20.2 \text{ mL Volume of undiluted } 0.5\text{N reagent required (mL)}$$

Volume of titrant was 1.7 mL to reach a final pH of 6.35

Final protein product met the acceptance criteria as follows:

Protein=5.0% pH=6.3

Polysorbate 80 on two tests ($A_{319}$) was 104.6 and 106.7; average was 105.7.

Methanol Content as measured by gas chromatogram was 32.4 ppm.

Example 1A

The 150 mM NaCl-Glycine buffer employed in Example 1 was prepared as follows:

The appropriate amount of buffer to prepare was calculated as follows:

$$[\text{Resuspended Paste Volume (L)} \times 10 \text{ L}] \times 2 + 60 = \text{Approx. Vol. of Buffer to prepare}$$

[13 L×10 L]×2+60=320 L of buffer to prepare

The amount of materials required were determined and measured to a calibrated depyrogenated container:

TABLE 2

| Material | Required Conc. × | Lot Size = | Required Amount |
|---|---|---|---|
| NaCl | 8.87 g/L | 320 L | 2,838.4 g |
| Aminoacetic Acid | 15.01 g/L | 320 L | 4,803.2 g |
| Polysorbate 80 | 0.02 g/L | 320 L | 6.4 g |

The polysorbate weighing vessel was rinsed several times with a total of approximately 2 liters of Water for Injection, U.S.P. and each rinse aliquot was added to the batch. A total of 10 L was added. The amount of the following materials were determined:

TABLE 3

| Material | Required Conc. × | Lot Size = | Required Amount |
|---|---|---|---|
| 1.0N NaOH | 0.125 ml/L | 320 L | 40 ml |

The admixture was diluted to volume with Water for Injection, U.S.P. and the final quantity was mixed for 60 minutes. The pH was determined; requirement was 6.3–6.5, The pH was 6.46. If the requirement was not met it is necessary to add 1.0N HCl or 1.0N NaOH until the required pH is obtained; the solution should be mixed for 15–30 minutes after each addition and the pH determination confirmed.

Digital Specific Conductance Determination was performed; the requirement at 25 C. is 14.15 to $15.59 \times 10^{-3}$ mhos/cm. The result was $15.38 \times 10^{-3}$ mhos/cm. If the requirements was not met it is necessary to discard and prepare fresh reagent.

The polysorbate 80 measurement was performed; the test sample must be 15 to 24 ppm polysorbate 80. The concentration was 22.8 ppm.

Example 2

Manufacture of virally-cleared RHOGAM® Rho(D) Immune Globulin (Human) by ultrafiltration proceeded as in Example 2 above with the following modifications:

Rho(D) Immune Globulin 6.802 Kg purified to step "Precipitate II paste" using the modified Cohn purification method was resuspended in 20.406 L of Water for Injection (WFI), U.S.P. cooled to 4 C. The admixture was vortexed (no foaming) for 4 hours, and stored at 4 C. until further use.

Following the SIP procedure, a VIRESOLVE® 180 SYSTEM Ultrafiltration System module (Millipore Corporation) (20 stack) for the approximately 27.208 L volume of resuspended Precipitate II volume was installed. Two BIOMAX™ 50 Filter cassettes were installed in place of the PELLICON® SYSTEM Filtration System CIP/SIP module. The VIRESOLVE® 180 SYSTEM Ultrafiltration System module was sanitized with chlorine and rinsed as described hereinabove. The BIOMAX™ 50 Filter membranes were flushed with WFI, U.S.P. Determination of Benzalkonium Chloride (Roccal) was performed on a final permeated flush sample; the benzalkonium chloride content was 8 ppm. A diffusion test was performed on the BIOMAX™ 50 Filter cassettes; release rate was calculated as described hereinabove; total volume released was 22 cc in 5 minutes, and the actual release rate was 4.4 cc/minute.

A viral clearance ultrafiltration using a VIRESOLVE® 180 SYSTEM Ultrafiltration System was performed on 245 L of the 50 mM NaCl Glycine buffer. The viral clearance recirculation tank (T1) was charged with 245 L of 50 mM NaCl-Glycine buffer. The buffer was recirculated in T1 while collecting the buffer permeate in the previously-sanitized 50 mM NaCl-Glycine buffer storage tank off line. Volume of permeated buffer collected was 213 L. Virally cleared buffer was stored at ambient temperature of about 63–78 F.

A 150 mM NaCl-Glycine buffer (see Example 2A for preparation) flush was performed by attaching the buffer feed tank to the viral clearance recirculation tank (T1). T1 was charged with 60 L of the 150 mM NaCl-Glycine buffer to flush.

The Precipitate II resuspension was processed as follows. The Precipitate II (6.802 Kg) was mixed at a speed creating a vortex without foaming, for 55 minutes, until completely suspended. Percent Protein by Refractive Index (mg/ml protein) was performed using hand held protometer on the Precipitate II resuspension, and was 59 mg/ml.

The required volume of diluted precipitate II was calculated to achieve a protein concentration of 5.0 mg/ml:

$$\frac{\text{Actual Ppt. II Vol. (L)} \times \text{Actual Protein Conc. (mg/ml)}}{5.0 \text{ mg/ml}} = \frac{\text{Req. Dil. Ppt. II}}{\text{Vol. (L)}}$$

OR $$\frac{(27.208 \text{ L}) \times (59.0 \text{ mg/ml})}{5.0} = 321.054 \text{ L Dil. Ppt. II vol.}$$

The required volume of 150 mM NaCl Glycine buffer was calculated using the following formula:

$$\text{Req. Dil. Ppt. II Vol. (L)} - \text{Resuspended Ppt. II Vol. (L)} = \text{Vol. buffer to add (L)}$$

OR (321.054 L)−(27.208 L)=293.846 L Buffer to add

The protein concentration was about 5.9%.

Buffer (293.846 L) was added to 27.208 L of diluted Precipitate II and mixed at a speed sufficient to create a vortex without foaming for 30 minutes.

The Viral clearance recirculation tank was charged with 107 L of diluted Ppt.II. The viral clearance recirculation tank (Pump No. 1) was started at a feed pump rate of 80% for the 20 stack VIRESOLVE® 180 SYSTEM Ultrafiltration System module being used. The viral clearance permeate pump flow rate (Pump No. 2) was ramped to 0.91 LPM (20%) for the 20 stack module to maintain an initial transmembrane pressure (TMP) of <1.6 psi. The actual pressure maintained was 1.2 psi. The product pump rate (Pump No. 3) was adjusted to level control rate. The TMP was maintained at <3.0 psi throughout the process by monitoring the protein concentration on the retentate side of the viral clearance recirculation tank. The in-line UV monitor was observed and maintained at a range of 6.4–7.7 absorbance units to correspond to a protein content on 4.5–5.5 mg/ml.

After approximately 75 L of permeate from the viral clearance tank was charged into the ultrafiltration tank (UF), the ultrafiltration feed pump (Pump No. 5) was started at 10%. The pump speed was increased (to 25%) until the UF permeate flow rate equals the flow rate of the viral clearance permeate, then set at 25% to maintain the volume. The UF permeate flow rate was 0.91 LPM and the VC permeate flow rate was 0.91 LPM. The UF tank constant volume maintained was 152 L. The UF Feed pressure was 4.0 psi, the UF permeate pressure 0.1 psi and the UF retentate pressure 0.7 psi.

Constant volume diafiltration was performed in T1 once the tank contained about 15–20 L. Diafiltration was maintained with a minimum of three buffer exchanges of 150 mM NaCl Glycine buffer (about 60 L total volume). The viral clearance tank pumps and mixer were turned off when the diafiltration was completed. The VC recirculation tank constant volume maintained was 15 L. The total buffer volume exchanged was 45 L.

The bulk in T2 was recirculated and thereby concentrated by constant volume diafiltration in T2, with the virally-cleared lot of 50 mM NaCl-Glycine buffer. The bulk was thereby concentrated to about the original starting volume of resuspended Ppt II. The permeate valve was fully open, and the UF feed pump rate was 70%; the feed pressure was maintained below 30 psi and the pressure differential maintained at 14–17 psi by applying back pressure to the retentate loop. The UF constant column maintained was 22 L and the total buffer volume exchanged was 121.2 L. A sample was drawn from T2 to perform a digital specific conductance determination on the UF permeate sample. The result was $5.47 \times 10^{-3}$ mhos/cm. Once the volume level was met, the UF permeate was shut off and the bulk mixed by recirculation, and a 10.5 ml sample was aseptically removed. Percent protein determination was made by refractive index using the hand held protometer on a 0.5 ml aliquot of the sample. The protein concentration was 7.9%.

The bulk from T2 was removed into an interim bulk vessel, and the full vessel weighed (gross weight) The bulk was returned to T2, and the empty interim bulk vessel was weighed:

Gross Weight (Kg)−Empty Vessel Weight (Kg)=Bulk Weight (Kg)

OR 58.180 (Kg)−25.24 Kg=32.94 Kg Bulk Weight

The required final volume of the bulk to achieve a 5% protein content was calculated as follows:

$$\frac{\text{Actual \% Protein} \times \text{Bulk Volume (L)}}{\text{Desired \% Protein (5.0\%)}} = \text{Required Final Vol (L)}$$

OR $$\frac{(7.9\%) \times (21.6 \text{ L})}{5.0\%} = 34.128 \text{ L Required Volume}$$

An initial pH determination was made on the remaining sample aliquot, by first diluting the aliquot 1:10 with 0.9% NaCl and titrated to a pH of 6.3–6.4 with 1:100 dilution of 0.5N HCl or 0.5N NaOH. pH was 6.55.

To adjust the pH, 1.35 mL of titrant 0.5N HCl in 0.9% NaCl was added, and the final pH was 6.35. If adjustment is required, the amount of undiluted 0.5N reagent required to adjust the pH of the bulk is calculated as follows:

$$\frac{\text{Required Final}}{\text{Volume (L)}} - \frac{\text{Volume of 1:100}}{\text{titrant required (ml)}} = \frac{\text{Volume of undiluted}}{0.5\text{N reagent (ml)}}$$

OR, in this case:

34.128 L×1.35 ml=46.1 ml undiluted 0.5N reagent

Integrity testing was performed on the VIRESOLVE® 180 SYSTEM Ultrafiltration System filter module in accordance with accepted methods. The integrity test value must be ≧1.2, and the module must be sanitized with chlorine as above and rinsed.

The required volume of 100× Thimerosol Solution was calculated:

$$\frac{\text{Required Final Bulk Volume (L)}}{100} = \frac{\text{Required Volume of 100}\times}{\text{Thimerosol solution (L)}}$$

OR 34.128 L=0.341 L of 100× Thimerosol Solution (L)

While constantly mixing the bulk, the 341 mL of 100× Thimerosol was added. The bulk was adjusted to the calculated required final volume with 0.801 L of virally-cleared 50 mM NaCl-Glycine Buffer and mixed for ten (10) minutes.

A 10.5 ml aliquot of bulk product was aseptically removed for determination of pH. pH must be 6.3–6.4. Actual pH on two readings was 6.38 and 6.345.
Final protein product met the acceptance criteria as follows:
Protein=5.3%
pH=as above
Methanol content as determined by gas chromatogram was 53.9 ppm
Polysorbate 80=101.7 ppm, 102.2 ppm on two tests; average was 101.9 ppm.

Example 2A

The 150 mM NaCl-Glycine buffer employed in Example 2 was prepared as follows:

The appropriate amount of buffer to prepare was calculated as follows:

$$[\text{Resuspended Paste Volume (L)} \times 10\text{L}] \times 2 + 60 = \begin{array}{l}\text{Approx. Vol.}\\\text{of Buffer to}\\\text{prepare}\end{array}$$

[27.208 L×10 L]×2+60=604.16 L of buffer to prepare

The amount of materials required were determined and measured to a calibrated depyrogenated container:

TABLE 4

| Material | Required Conc. × | Lot Size = | Required Amount |
|---|---|---|---|
| NaCl | 8.87 g/L | 604.16 L | 5,358.90 g |
| Aminoacetic Acid | 15.01 g/L | 604.16 L | 9,068.44 g |
| Polysorbate 80 | 0.02 g/L | 604.16 L | 12.08 g |

The polysorbate weighing vessel was rinsed several times with a total of approximately 2 liters of Water for Injection, U.S.P. and each rinse aliquot was added to the batch, and qs to 604.16 L. The amount of the following materials were determined:

TABLE 5

| Material | Required Conc. × | Lot Size = | Required Amount |
|---|---|---|---|
| 1.0N NaOH | 0.125 ml/L | 604.16 L | 75.52 ml |

The admixture was diluted to volume with Water for Injection, U.S.P. and the final quantity was mixed for 60 minutes. The pH was determined; requirement was 6.3–6.5, The pH was 6.38. If the requirement was not met it is necessary to add 1.0N HCl or 1.0N NaOH until the required pH is obtained; the solution should be mixed for 15–30 minutes after each addition and the pH determination confirmed.

Digital Specific Conductance Determination was performed; the requirement at 25 C. is 14.15 to 15.59×10$^{-3}$ mhos/cm. The result was 15.18×10$^{-3}$ mhos/cm. If the requirements was not met it is necessary to discard and prepare fresh reagent.

The polysorbate 80 measurement was performed; the test sample must be 15 to 24 ppm polysorbate 80. The concentration was 19.5 ppm.

Comparative Examples

Polysorbate 80 Versus No Polysorbate 80

Comparative Example 1A—Containing Polysorbate 80

Precipitate II paste (10 g) was suspended in 30 ml of WFI. Such resuspended paste (40 ml) was admixed with 360 ml of 150 mM NaCl-Glycine buffer (diluting 10×) containing 100 ppm (0.1 g/L) Polysorbate 80 for a total volume of 400 ml. Permeate flow through the Millipore Multiplex pumping platform (⅓ sq. ft. module) was run at 21.8 ml/minute while flux was 0.06 ml/min./cm sq. After 39 minutes of running, the transmembrane pressure remained below 1.3 psi with the sieving coefficient greater than 80%. Free passage of the IgG polyclonal anti-D material was insured using high ionic strength buffer system with polysorbate 80.

Comparative Example 1B—Containing No Polysorbate 80

Precipitate II paste (10 g) was suspended in 30 ml of WFI. Such resuspended paste (40 ml) was admixed with 360 ml of 150 mM NaCl-Glycine buffer (diluting 10×) containing no polysorbate 80, for a total volume of 400 ml. Permeate flow through the Millipore Multiplex pumping platform (⅓ sq. ft. module) was run at 21.8 ml/minute while flux was 0.06 ml/min./cm sq. After 39 minutes of running, the transmembrane pressure was at 6.1 psi with the sieving coefficient rapidly reduced to approximately 60%. Free passage of the IgG polyclonal anti-D material was insured using high ionic strength buffer system with polysorbate 80.

Results of this comparative study show the necessity for presence polysorbate 80 in the high ionic strength buffer system.

Comparative Example 2

Low Ionic Strength Versus High Ionic Strength Buffer

Comparative Example 2A—Low Ionic Strength Buffer

Precipitate II paste (1.35 g) was suspended in 4.5 ml of WFI. Such resuspended paste (5.0 ml) was admixed with 45 ml of 50 mM NaCl-Glycine buffer containing 0.1 g/L polysorbate 80, for a total volume of 50 ml. Permeate flow through the VIRESOLVE® 180 SYSTEM Ultrafiltration System Small Area Module (SAM, 10 sq.cm.) (Millipore Corporation, Bedford, Mass.) was run at cross flow of 15.6 ml/minute while flux was 0.64 ml/min./cm sq. After 28 minutes of running, the sieving coefficient rapidly reduced to approximately 31%.

Comparative Example 2B—High Ionic Strength Buffer

Resuspended precipitate II paste (46.0 ml) in 50 mM NaCL-glycine buffer containing 100 ppm (0.01%) polysorbate 80 from Comparative Example 2A, to which 0.29 g of NaCl had been added bringing it to 150 mM NaCl-glycine buffer was employed. Permeate flow through the VIRESOLVE® 180 SYSTEM Ultrafiltration System Small Area Module (SAM, 10 sq.cm.) (Millipore Corporation, Bedford, Mass.) was run at 15.6 ml/minute while flux was 0.64 ml/min./cm sq. After 40 minutes of running, the sieving coefficient at 86%.

Results of this comparative study of low versus high ionic strength buffer systems as disclosed in Comparative Examples 2A and 2B demonstrates that the ionic concentration of the buffering system during processing has a measurable and significant impact on the protein's passage point through the Viresolve membrane.

Comparative Example 3

Lyophilized Precipitate II Paste Product Dissolved in WFI, Low Ionic Strength

Summary

A human IgG product was tested with the VIRESOLVE® 180 SYSTEM Ultrafiltration System ⅓ ft$^2$ module to determine the performance attributes of the membrane with this molecule. Two types of experiments were conducted; flux excursion and volume reduction. The initial testing provided basic membrane data by measuring the protein sieving as a function of flux. The data from the flux excursion were used for the volume reduction experiment to mimic a process run. No protein passage was seen during the flux excursion for the product in Water For Injection (WFI). The subsequent experiments utilized the product in glycine buffer (containing 0.01% polysorbate-80). A protein mass recovery of 89.1% was achieved using this solution with an 83.3% volume increase.

Objective

The experiments were performed to evaluate the sieving coefficient and protein mass recovery of the product when processed through the VIRESOLVE® 180 SYSTEM Ultrafiltration System module. The data generated by these experiments were used to determine system operating conditions.

Experimental

The initial experiment was conducted in a cold room at 4° C. using the product dissolved in WFI. All subsequent experiments were conducted at room temperature with ⅓ ft$^2$ VIRESOLVE® 180 SYSTEM Ultrafiltration System modules. All total protein concentrations were determined by reading the optical density (O.D.) at 280 nm. All samples were diluted in and read against product buffer.

Flux Excursion

Figure 3A:
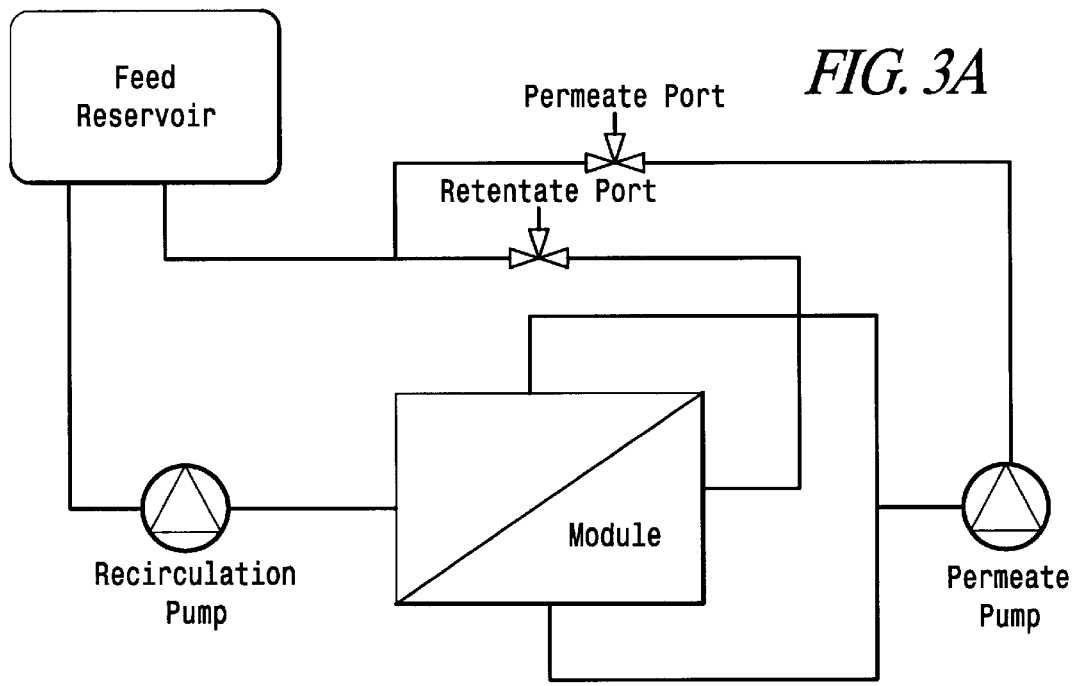
FIG. 3A is a schematic of the VIRESOLVE® 180 SYSTEM Ultrafiltration System as assembled for the Comparative Example 3 comprising low ionic strength buffer and polysorbate-80.

1) The system was assembled as shown in FIG. 3A using VIRESOLVE® 180 SYSTEM Ultrafiltration System module #0010 from lot #K2EM0536 (Millipore Corporation, Bedford, Mass.).
2) 500 mL of Precipitate II lyophilized powder that had been lyophilized in WFI, at a concentration of approximately 1% protein, was pumped into a 1000 mL capacity feed bag. A sample of the product was taken to determine the initial protein concentration. The bag was connected to the system and the tubing was primed to remove air.
3) The product was recirculated for 30 minutes at a cross flow rate of 500 mL/min. (Permeate pump was off.)
4) A 1 mL sample was drawn from the retentate port to determine if significant protein adsorption had occurred (R0). Note: All samples taken were 1 mL unless otherwise noted.
5) Permeate flow was initiated at a flow rate of 1.09 mL/min (J=0.003 mL/min/cm$^2$). Permeate flow was controlled by a Watson Marlow 503U pump with a 308MC/A pump head. Product was recirculated back to the feed loop for 35 minutes.
6) After the 35 minute recirculation, one retentate (R1) and one permeate (P1) sample were collected. At this point, the process was removed from the cold room and placed at room temperature. The recirculation was continued at the same flow rates for 30 minutes.
7) After the 30 minute recirculation at room temperature, one retentate (R2) and one permeate (P2) were collected.
8) The cross flow was then increased to approximately 600 mL/min and allowed to recirculate for 15 minutes. One retentate (R3) and one permeate (P3) sample were collected.
9) The product was diluted to 0.5% with the product buffer. The cross flow rate and the permeate flow rate remained constant. One retentate (R4) and one permeate (P4) were collected after a 20 minute recirculation.
10) Two additional permeate flux rates were tested. 0.005 mL/min/cm$^2$ (1.82 mL/min) and 0.01 mL/min/cm$^2$ (3.63 mL/min). Each was allowed to recirculate for at least 30 minutes.

Combined Flux Excursion and Volume Reduction

Figure 3B:
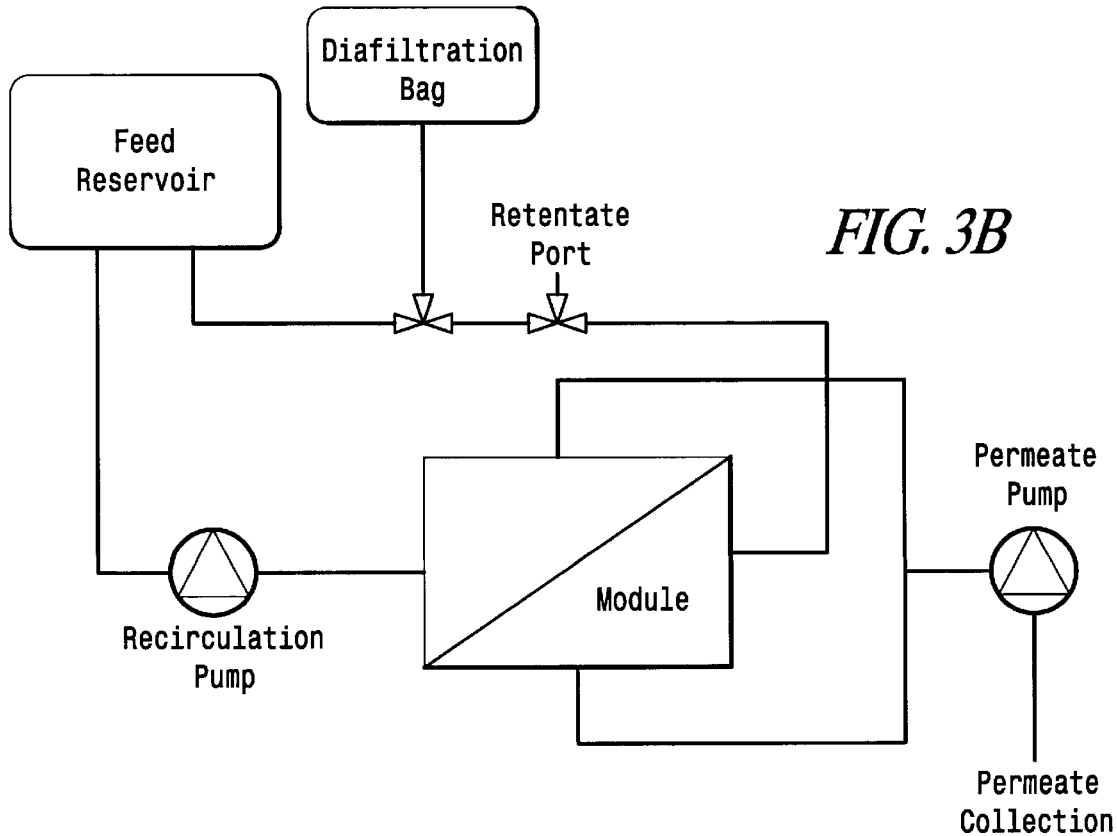
FIG. 3B is a schematic of the re-configured VIRESOLVE® 180 SYSTEM Ultrafiltration System after the conclusion of the flux excursion portion of Comparative Example 3.

A second experiment was performed on the human IgG dissolved in glycine buffer.
1) The system was assembled as shown in FIG. 3A using VIRESOLVE® 180 SYSTEM Ultrafiltration System module #0009 from lot #K2EM0536.
2) 990 mL of product at approximately 0.1% were pumped into a 1 L capacity feed bag. A 1 mL sample was drawn to determine the actual protein concentration. Note: All samples taken were 1 mL unless otherwise noted. The bag was connected to the system and the tubing was primed to remove air.
3) The product was recirculated for 30 minutes at a cross flow rate of 50 mL/min. (Permeate pump was off). Cross flow rate was controlled by a Watson Marlow 503U pump with a 501RL pump head. After recirculation, a sample (R0) was collected to test for protein adsorption.
4) Four permeate flux rates were tested: 0.003, 0.005, 0.030, and 0.050 mL/min/cm$^2$. The product was allowed to recirculate for 30 minutes at each permeate flux rate. The cross flow was increased to 600 mL/min for the 0.05 mL/min/cm$^2$ flux rate. After 30 minutes, one permeate and one retentate sample were drawn.
5) After the conclusion of the flux excursion portion of the experiment the permeate pump was shut off. The system was reconfigured as seen in FIG. 3B. An initial sample was drawn of 15 mL.
6) The product was then processed at a flux of 0.05 mL/min/cm$^2$ (18.2 mL/min). Note: The measured flux was 0.043 mL/min/cm$^2$ (15.7 mL/min).
7) Retentate and permeate samples were collected at 100, 250, and 500 mL of product processed.
8) Diafiltration (at the permeate flow rate) with the product buffer was initiated after processing 645 mL of the IgG solution. This diafiltration continued for a total of 500 mL processed through the VIRESOLVE® SYSTEM Ultrafiltration System module. Retentate and permeate samples were collected at 745, 895, and 1145 mL processed.
9) The remaining solution was processed in the volume reduction mode down to the hold-up volume of the system. Retentate and permeate samples were taken at 1245, and 1475 mL of total processed volume.
10) A final diafiltration step was performed to recover product concentrated in the hold-up volume. Diafiltration was continued for a total of four, 50 mL volumes. Each diafiltration volume was collected separately.
11) A sample of the pooled, bulk permeate and a sample from each pooled diafiltration volume was collected. A final retentate sample was also drawn at the conclusion of the experiment to determine the concentration of the product remaining in the feed bag.

Results

Flux Excursion

No product passage was observed during the initial flux excursion experiment. The process was placed at room temperature (initially at 4° C.) in a effort to improve product solubility. No increase in product passage was seen. Other methods of inducing protein passage included raising the cross flow, diluting the product, and increasing the permeate flux rate to force protein passage. The sieving coefficient remained zero for all of the test conditions.

The initial product sample was suspended in WFI. The solution appeared hazy and a solubility problem as suspected. Additional product was then dissolved in glycine buffer; this solution was used for the remainder of the testing.

Combined Flux Excursion and Volume Reduction

Table 6 displays the results of the flux excursion experiment performed on the IgG suspended in glycine buffer. The table represents data collected on product at approximately 0.1% total protein. The table presents product concentration values in terms of absorbance units (AU). A dilution factor has been calculated into the values.
Initial Concentration: 1.68 AU
R0 Concentration: 1.81 AU

TABLE 6

| Flux mL/min/cm$^2$ | Concentration Retentate | Permeate | Sieving Coefficient (%) | 1/Conversion |
|---|---|---|---|---|
| 0.003 | 1.80 | 0.88 | 48.9 | 458.7 |
| 0.005 | 1.97 | 0.89 | 45.2 | 264.6 |
| 0.030 | 1.96 | 1.05 | 53.6 | 45.9 |
| 0.050 | 1.99 | 1.07 | 53.8 | 27.5 |

Figure 4:
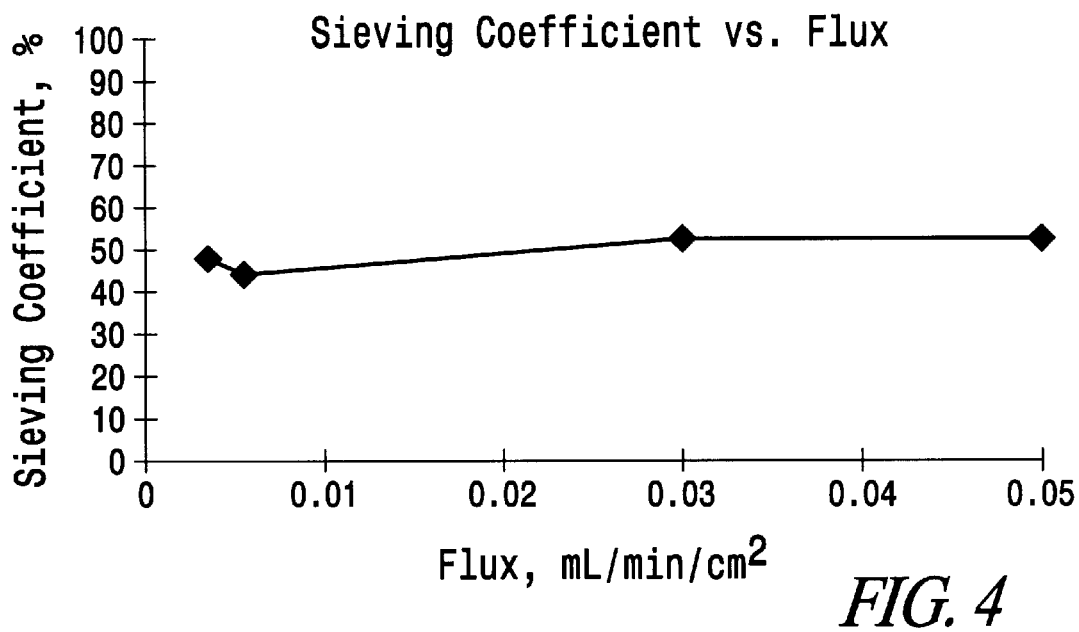
FIG. 4 is a graph depicting sieving coefficient vs. flux for the immunoglobulin G in low ionic strength buffer in the flux excursion experiment of Comparative Example 3.

The sieving coefficient versus flux curve for the IgG in glycine buffer is plotted in FIG. 4.

The following are the product concentration data (AU) from the volume reduction experiment.

| | |
|---|---|
| Initial Process Volume: | 963 mL |
| Initial Concentration: | ~0.1% (1.80 AU) Total Protein |
| Cross Flow Rate: | 600 mL/min |
| Measured Flux: | 0.043 mL/min/cm$^2$ |
| | (Flow Rate: 15.7 mL/min) |
| Bulk 1 Permeate Volume: | 645 mL |
| Process Diafiltration Volume: | 500 mL |
| Bulk 2 Permeate Volume: | 330 mL |

Table 7 provided the protein concentration and sieving coefficient data collected during the volume reduction experiment. The table presents product concentration values in terms of absorbance units (AU). A dilution factor has been calculated into the values.

TABLE 7

| Volume Processed (mL) | Concentration (AU) Retentate | Permeate | Sieving Coefficient (%) |
|---|---|---|---|
| 100 | 1.80 | 1.04 | 57.8 |
| 250 | 2.02 | 1.03 | 51.0 |
| 500 | 2.55 | 0.99 | 38.8 |
| 745* | 3.03 | 1.07 | 35.3 |
| 895* | Dilution Error | Dilution Error | — |
| 1145* | 1.97 | 0.54 | 27.4 |
| 1245 | 2.34 | 0.63 | 26.9 |
| 1475 | Dilution Error | 0.99 | — |

Table 8 provides the total protein concentration data from each step of the volume reduction experiment. A dilution factor has been calculated into the values.

TABLE 8

| Process Step | Total Volume (mL) | Concentration (AU/mL) |
|---|---|---|
| Bulk 1 Permeate | 645 | 1.15 |
| Process Diafiltration | 500 | 0.81 |
| Bulk 2 Permeate | 330 | 0.68 |
| 1st Diafiltration | 53 | 0.84 |
| 2nd Diafiltration | 60 | 0.59 |
| 3rd Diafiltration* | 50 | 0.50 |

TABLE 8-continued

| Process Step | Total Volume (mL) | Concentration (AU/mL) |
|---|---|---|
| 4th Diafiltration | 100* | 0.44 |

*4th Diafiltration plus final volume reduction.

Figure 5:
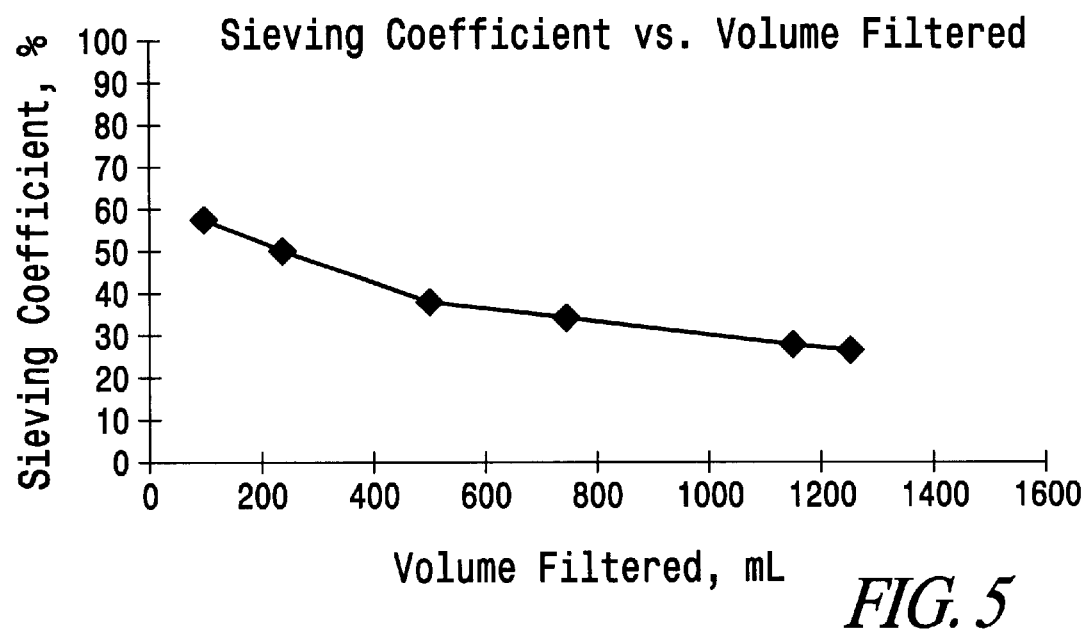
FIG. 5 is a graph depicting sieving coefficient vs. volume filtered for the immunoglobulin G in low ionic strength buffer in the volume reduction experiment of Comparative Example 3.

The sieving coefficient versus volume filtered curve for the volume reduction experiment is plotted in FIG. 5.

Discussion

Protein Mass Recovery $$\text{Recovery} = \frac{(\text{mg protein process}) + (\text{mg protein diafiltration}) + (\text{mg protein permeate samples})}{(\text{mg protein initial}) - (\text{mg protein retentate samples})}$$

TABLE 9

Volume Reduction

| Process Step | Total Volume (mL) | Concentration (AU/mL) | Protein Mass (AU) |
|---|---|---|---|
| Initial | 963 | 1.80 | 1733.4 |
| Bulk 1 Permeate | 645 | 1.15 | 741.8 |
| Process Diafiltration | 500 | 0.81 | 405.0 |
| Bulk 2 Permeate | 330 | 0.68 | 224.4 |
| 1st Diafiltration | 53 | 0.84 | 44.5 |
| 2nd Diafiltration | 60 | 0.59 | 35.4 |
| 3rd Diafiltration | 50 | 0.50 | 25.0 |
| 4th Diafiltration* | 100 | 0.44 | 44.0 |

*4th Diafiltration plus final volume reduction.

Total Protein Mass of Retentate Samples: 20.6 AU
Total Protein Mass of Permeate Samples: 6.2 AU $$\text{Recovery with no diafiltration} = \frac{(741.8 \text{ AU} + 405.0 \text{ AU} + 224.4 \text{ AU} + 6.2 \text{ AU})}{(1733.4 \text{ AU} - 20.6 \text{ AU})} 100 = 80.4\%$$

$$\text{Recovery with one diafiltration} = \frac{(1377.4 \text{ AU} + 44.5 \text{ AU})}{(1733.4 \text{ AU} - 20.6 \text{ AU})} 100 = 83.0\%$$

$$\text{Recovery with two diafiltration} = \frac{(1377.4 \text{ AU} + 44.5 \text{ AU} + 35.4 \text{ AU})}{(1733.4 \text{ AU} - 20.6 \text{ AU})} 100 = 85.1\%$$

$$\text{Recovery with three diafiltration} = \frac{(1377.4 \text{ AU} + 44.5 \text{ AU} + 35.4 \text{ AU} + 25.0 \text{ AU})}{(1733.4 \text{ AU} - 20.6 \text{ AU})} 100 = 86.6\%$$

$$\text{Recovery with three diafiltration} = \frac{(1377.4 \text{ AU} + 44.5 \text{ AU} + 35.4 \text{ AU} + 25.0 \text{ AU} + 44.0 \text{AU})}{(1733.4 \text{ AU} - 20.6 \text{ AU})} 100 = 89.1\%$$

Diafiltration provides greater protein mass recovery but results in increased product volume and product dilution. The percent volume increases for each diafiltration step are as follows:

Process Diafiltration: 55.7% volume increase
1 Final Diafiltration: 61.3% volume increase
2 Final Diafiltration: 67.6% volume increase
3 Final Diafiltration: 72.8% volume increase
4 Final Diafiltration: 83.3% volume increase On the basis of the protein sieving data produced by the experiments, the following information was learned:

1) Protein adsorption to the VIRESOLVE® 180 SYSTEM Ultrafiltration System appears to be negligible.
2) The haze seen in the solution of product suspended in WFI plus the fact that there was no protein passage with this solution, indicate that there is a stability issue with this product and WFI. Protein passage through the VIRESOLVE® 180 SYSTEM Ultrafiltration System membrane was achieved with the protein suspended in glycine buffer.
3) The sieving coefficient drops steadily as the protein is concentrated on the upstream side of the membrane during processing.
4) The low sieving coefficient at the end of the process (~25%) indicates that significant protein polarization is occurring on the membrane surface.

Conclusions

The feasibility study was performed with the VIRESOLVE® 180 SYSTEM Ultrafiltration System membrane using the human IgG product suspended in two different buffers: WFI, and glycine buffer. No protein passage was seen using the product suspended in WFI. There was a slight haze associated with the starting solution indicating that the protein was not fully in solution. This would cause immediate polarization of the membrane, blocking the membrane to protein passage. The results of the flux excursion suggest that this is indeed what happened; the undissolved protein blinded the membrane prohibiting protein passage.

There was a marked difference in the clarity of the solution containing product in glycine buffer; this solution was not hazy. The flux excursion for this solution provided a sieving coefficient at approximately 50% for all of the flux rates tested (0.003 mL/min/cm² to 0.5 mL/min/cm²). The concentration of the product in glycine buffer was approximately 0.1% (total protein).

The 0.1% solution was used to perform the volume reduction experiment. A product recovery of 89.1% was achieved with an 83.3% volume increase. An in process diafiltration step was utilized in an effort to limit the protein concentration on the upstream side of the membrane during processing. A final diafiltration step was also used to recover the protein in the hold-up volume of the system.

The sieving coefficient dropped steadily during the process from an initial sieving coefficient of 57.8% to a final sieving coefficient of 26.9%. This indicates that a substantial protein layer builds on the membrane during processing. The mid-process diafiltration slowed the drop in the sieving coefficient, but did not increase it or hold it steady. The final diafiltration step did recover some of the protein from the hold-up volume and the membrane surface. The protein concentration of these final diafiltration volumes was approximately 25 to 50% of the initial starting solution; this indicates that the fresh buffer wash of diafiltration slowly removes the protein polarization layer of the membrane. It is desirable to have more product come off the membrane during diafiltration, this reduces product dilution and process time. An extended final diafiltration would recover more protein, but would cause greater product dilution.

The product as tested had 5–12% dimers in solution. These dimers consist of active product. The presence of dimers would undoubtedly cause protein polarization on the membrane surface and the dimers, if they remained intact, would be trapped upstream.

This Comparative Example shows that under the conditions utilizing lyophilized starting material and low ionic strength buffer, a lower sieving coefficient was obtained, demonstrating that even at highly diluted conditions, the protein passes through the filter at less than 50% efficiency. Equipment containing much larger filter area would be required to process this material in the same amount of time as provided for in the optimized, validatable process of Examples 1 and 2.

It will be understood by those skilled in the art that the foregoing description and examples are illustrative of practicing the present invention, but are in no way limiting. Variations of the detail presented herein may be made without departing from the scope and spirit of the present invention.

What is claimed is:

1. A method for making a substantially pure, virus free immunoglobulin formulation comprising the steps of:
   (a) admixing an immunoglobulin fraction isolated from human plasma with a high ionic strength buffer containing a non-ionic detergent;
   (b) performing nanofiltration on the admixture using a less than about 30 nm nanofilter; and
   (c) collecting permeate of the nanofiltration, wherein said permeate is substantially pure, virus free immunoglobulin, wherein said immunoglobulin has a molecular weight of about 180 kilodaltons or less.

2. The method of claim 1 wherein the cutoff rating is about 12 nm.

3. The method of claim 1 wherein the immunoglobulin is present in the admixture at a concentration of 0.1–1%.

4. The method of claim 1 wherein the immunoglobulin is present in the admixture at a concentration of about 0.5%.

5. The method of claim 1 wherein the buffer is 150 mM NaCl-Glycine+/−20% buffer.

6. The method of claim 1 wherein the buffer is pH 6.4.

7. The method of claim 1 wherein the buffer is 150 mM NaCl-Glycine+/−20% pH 6.4 buffer.

8. The method of claim 1 wherein the non-ionic detergent is at a concentration of 0.015 g/L to about 0.024 g/L.

9. The method of claim 1 wherein the non-ionic detergent is at a concentration of about 0.02 g/L.

10. The method of claim 1 wherein the non-ionic detergent is at a concentration at the critical micelle concentration.

11. The method of claim 1 wherein the non-ionic detergent is at a concentration within the critical micelle concentration.

12. The method of claim 1 wherein the non-ionic detergent is at a concentration of about 80–200 ppm.

13. The method of claim 1 wherein the non-ionic detergent is at a concentration of about 100 ppm.

14. The method of claim 1 wherein the immunoglobulin fraction is isolated from human plasma by batch chromatography, ionic exchange chromatography or affinity chromatography.

15. The method of claim 1 wherein the immunoglobulin fraction is isolated from human plasma by an alcohol fractionation process.

16. The method of claim 1 wherein the immunoglobulin fraction is isolated from human plasma by an alcohol fractionation process, wherein the alcohol is methanol.

17. The method of claim 1 wherein the non-ionic detergent is a non-ionic polyoxyethylene detergent.

18. The method of claim 1 wherein the buffer is 150 mM NaCl-Glycine buffer.

19. The method of claim 18 wherein the non-ionic detergent is at a concentration of 0.015 g/L to about 0.024 g/L.

20. The method of claim 18 wherein the non-ionic detergent is at a concentration of about 0.02 g/L.

21. The method of claim 18 wherein the non-ionic detergent is a non-ionic polyoxyethylene detergent.

22. The method of claim 21 wherein the non-ionic polyoxyethylene detergent is polysorbate-80.

23. The method of claim 22 wherein the permeate is further processed using a second nanofilter having a cutoff rating of about 10 kilodaltons to about 60 kilodaltons; wherein substantially pure immunoglobulin is retained in the retentate following processing with the second nanofilter.

24. The method of claim 23 wherein the cutoff rating of the second nanofilter is about 50 kilodaltons.

25. The method of claim 24 wherein the immunoglobulin is anti-D immunoglobulin.

26. The method of claim 25 wherein said substantially pure anti-D immunoglobulin is used to prepare a solution containing 300 micrograms of said anti-D immunoglobulin.

27. The method of claim 25 wherein said substantially pure anti-D immunoglobulin is used to prepare a solution containing 50 micrograms of said anti-D immunoglobulin.

28. A process for the manufacture of substantially pure, virus-free immunoglobulin comprising anti-D antibody, said process comprising the steps of:
   (a) admixing an immunoglobulin fraction comprising anti-D antibody isolated from human plasma with a high ionic strength buffer containing a non-ionic detergent;
   (b) performing nanofiltration on the admixture using a less than about 30 nm nanofilter; and
   (c) collecting permeate of the nanofiltration, wherein said permeate is substantially pure, virus-free immunoglobulin having a molecular weight of about 180 kilodaltons or less, and comprising anti-D antibody.

29. The process of claim 28 wherein the high ionic strength buffer comprises 150 mM NaCl-Glycine buffer and the non-ionic detergent comprises polysorbate 80.

30. The method of claim 28 wherein the cutoff rating is about 12 nm.

31. The process of claim 30 wherein the permeate is further processed using a second nanofilter having a cutoff rating of about 10 kilodaltons to about 60 kilodaltons; wherein substantially pure immunoglobulin is retained in the retentate following processing with the second nanofilter.

32. The process of claim 31 wherein the cutoff rating of the second nanofilter is about 50 kilodaltons.

33. The process of claim 28 further comprising the step of concentrating the immunoglobulin in a low ionic strength buffer by further processing said permeate using a second nanofilter having a cutoff rating of about 50 kilodaltons; wherein substantially pure immunoglobulin is retained in the retentate following processing with the second nanofilter, said substantially pure immunoglobulin retained in the retentate following processing with the second nanofilter is present at a higher concentration than said substantially pure immunoglobulin collected in the permeate according to step (c), and said buffer in the retentate is a low ionic strength buffer.

34. The process of claim 33 wherein the low ionic strength buffer is 50 mM NaCl-Glycine buffer.

35. The process of claim 28 wherein the immunoglobulin is present in the admixture at a concentration of 0.1–1%.

36. The process of claim 28 wherein the buffer is 150 mM NaCl-Glycine+/−20% buffer.

37. The process of claim 28 wherein the non-ionic detergent is at a concentration of 0.015 g/L to about 0.024 g/L.

38. The process of claim 28 wherein the non-ionic detergent is at a concentration within the critical micelle concentration.

39. The process of claim 28 wherein the non-ionic detergent is at a concentration of about 80–200 ppm.

40. The process of claim 28 wherein the immunoglobulin fraction is isolated from human plasma by batch chromatography, ionic exchange chromatography, affinity chromatography, or alcohol fractionation.

41. The process of claim 28 wherein the non-ionic detergent is a non-ionic polyoxyethylene detergent.

42. The process of claim 28 wherein the non-ionic detergent is a polysorbate 80.

43. A process for the manufacture of substantially pure protein comprising the steps of:
   (a) isolating a protein from plasma;
   (b) admixing the isolated protein with high ionic strength buffer containing a non-ionic detergent;
   (c) performing nanofiltration on the admixture using a less than about 30 nm nanofilter; and
   (d) collecting permeate from the nanofiltration, wherein said permeate is substantially pure protein wherein said protein has a molecular weight of 180 kilodaltons or less.

44. The process of claim 43 wherein the protein is an immunoglobulin.

45. The process of claim 43 wherein the isolating step (a) is selected from the group consisting of batch chromatography, ionic exchange chromatography, affinity chromatography or alcohol fractionation.

46. A method for making a substantially pure IgG immunoglobulin formulation comprising the steps of:
   (a) admixing an IgG immunoglobulin fraction isolated from human plasma with a high ionic strength buffer containing a non-ionic detergent;
   (b) performing nanofiltration on the admixture using a less than about 30 nm nanofilter; and
   (c) collecting permeate of the nanofiltration, wherein said permeate is substantially pure IgG immunoglobulin.

47. The method of claim 46 wherein the IgG immunoglobulin is present in the admixture at a concentration of 0.1–1%.

48. The method of claim 46 wherein the IgG immunoglobulin is present in the admixture at a concentration of 0.5%.

49. The method of claim 46 wherein the buffer is 150 mM NaCl-Glycine+/−20% buffer.

50. The method of claim 46 wherein the buffer is 150 mM NaCl-Glycine buffer.

51. The method of claim 46 wherein the buffer is 150 mM NaCl-Glycine+/−20% buffer pH 6.4.

52. The method of claim 46 wherein the buffer is pH 6.4.

53. The method of claim 46 wherein the non-ionic detergent is at a concentration of 0.015 g/L to about 0.024 g/L.

54. The method of claim 46 wherein the non-ionic detergent is at a concentration of about 0.02 g/L.

55. The method of claim 46 wherein the non-ionic detergent is at a concentration at the critical micelle concentration.

56. The method of claim 46 wherein the non-ionic detergent is at a concentration within the critical micelle concentration.

57. The method of claim 46 wherein the non-ionic detergent is at a concentration of about 80–200 ppm.

58. The method of claim 46 wherein the non-ionic detergent is at a concentration of about 110 ppm.

59. The method of claim 46 wherein the non-ionic detergent is a non-ionic polyoxyethylene detergent.

60. The method of claim 46 wherein the non-ionic detergent is polysorbate 80.

61. The method of claim 46 wherein the polysorbate-80 is at a concentration of 0.015 g/L to about 0.024 g/L.

62. The method of claim 46 wherein the polysorbate-80 is at a concentration of 0.02 g/L.

63. The method of claim 46 wherein the nanofilter is about 12 nm nanofilter.

64. The method of claim 46 wherein the permeate is further processed using a second nanofilter having a cutoff rating of about 10 kD to about 60 kD; wherein substantially pure IgG immunoglobulin is retained in the retentate following processing with the second nanofilter.

65. The method of claim 64 wherein the cutoff rating of the second nanofilter is about 50 kD.

66. The method of claim 46 wherein the IgG immunoglobulin is anti-D immunoglobulin.

67. The method of claim 46 wherein the immunoglobulin fraction is isolated from human plasma by batch chromatography, ionic exchange chromatography or affinity chromatography.

68. The method of claim 46 wherein the immunoglobulin fraction is isolated from human plasma by an alcohol fractionation process.

69. The method of claim 46 wherein the immunoglobulin fraction is isolated from human plasma by an alcohol fractionation process, wherein the alcohol is methanol.

70. A method for making a substantially pure IgG immunoglobulin formulation comprising the steps of:
   (a) admixing an IgG immunoglobulin fraction isolated from human plasma with 150 mM NaCl-Glycine buffer containing about 0.002% w/v polysorbate-80, wherein said IgG immunoglobulin is present in said admixture at a concentration of 0.1–1.0%;
   (b) performing nanofiltration on the admixture using a less than about 30 nm nanofilter; and
   (c) collecting permeate of the nanofiltration, wherein said permeate is substantially pure IgG immunoglobulin.

71. The method of claim 70 wherein the nanofilter is about 12 nm nanofilter.

72. The method of claim 70 wherein the permeate is further processed using a second nanofilter having a cutoff rating of about 10 kD to about 60 kD; wherein substantially pure IgG immunoglobulin is retained in the retentate following processing with the second nanofilter.

73. The method of claim 72 wherein the cutoff rating of the second nanofilter is about 50 kD.

74. The method of claim 70 wherein the IgG immunoglobulin is anti-D immunoglobulin.

75. The method of claim 70 wherein the IgG immunoglobulin fraction is isolated from human plasma by an alcohol fractionation process comprising the steps of:

cooling whole human plasma to about 1° C.;

centrifuging said cooled plasma to separate a cold insoluble precipitate from a supernatant;

adding cold alcohol to said supernatant and centrifuging to separate a Precipitate I from a Supernatant I;

adding cold alcohol to said Supernatant I and centrifuging to separate a Precipitate II+III from a Supernatant II+III;

adding cold alcohol to said Precipitate II+III and centrifuging to separate a Precipitate II+III W from a Supernatant II+III W;

adding cold alcohol to said Precipitate II+III W and centrifuging to separate a Precipitate III from a Supernatant III;

filtering Supernatant III, adjusting the filtrate by addition of cold alcohol, and centrifuging the adjusted filtrate to separate a Precipitate II from a Supernatant II; wherein the Precipitate II is essentially pure gamma G globulin.

76. The method of claim 70 wherein the alcohol is methanol.

77. The method of claim 76 wherein the IgG immunoglobulin fraction is isolated from human plasma by an alcohol fractionation process comprising the steps of:

cooling human plasma to about 1° C., and separating from said plasma a first supernatant and a first precipitate;

adding methanol to said first supernatant and adjusting the temperature to about −2° C., the amount of said methanol being between 10.5% and 10.9%, the pH being between 7 and 74 and the ionic strength being 0.136 gi/liter and separating from the resulting liquid system a second precipitate and a second supernatant;

adding methanol to said second supernatant and adjusting the temperature to about −5° C., the amount of said methanol being between 33.25% and 33.35%, the pH being between 6.7 and 7.1 and the ionic strength being between 0.081 and 0.091 gi/liter and separating from the resulting liquid system a third precipitate and a third supernatant;

adding methanol to said third precipitate and adjusting the temperature to about −5° C., the amount of said methanol being between 26.5% and 26.9%, the pH being between 7.0 and 7.4 and the ionic strength being between 0.0047 and 0.0057 gi/liter and separating from the resulting liquid system a fourth precipitate and a fourth supernatant;

adding methanol to said fourth precipitate and adjusting the temperature to about −6° C., the amount of said methanol being between 22.5% and 22.9%, the pH being between 5.0 and 5.4 and the ionic strength being between 0.008 and 0.018 gi/liter and separating from the resulting liquid system a fifth precipitate and a fifth supernatant;

adding methanol to said fifth supernatant and adjusting the temperature to about −6.5° C., the amount of said methanol being between 33.0% and 33.4%, the pH being between 7.0 and 7.4 and the ionic strength being between 0.055 and 0.065 gi/liter and separating said resulting liquid into a sixth precipitate and a sixth supernatant.

* * * * *

UNITED STATES PATENT AND TRADEMARK OFFICE
CERTIFICATE OF CORRECTION

PATENT NO. : 6,096,872
DATED : August 1, 2000
INVENTOR(S) : Van Holten et al.

It is certified that error appears in the above-identified patent and that said Letters Patent is hereby corrected as shown below:

Title page,
Item [56], OTHER PUBLICATIONS, "Value of Virus Filtration...., Vox Sang, 1996; 70:235-236" please delete "Plasmaa" and insert therefor -- Plasma --;

Column 10,
Lines 30 & 34, please delete "d" and insert therefor -- $\leq$ --;

Column 13,
Line 18, please insert under (50mM NaCl-Glycine) -- Buffer Required to Add (L) --;
Line 32, please delete "Viresolve-180" and insert therefor -- VIRESOLVE® 180 SYSTEM Ultrafiltration System --;

Column 17,
Line 34, please delete "e1.2," and insert therefor -- $\geq$1.2, --;

Column 32,
Line 14, please delete "110 ppm" and insert therefor -- 100 ppm --;

Column 33,
Line 31, please delete "74" and insert therefor -- 7.4 --;

Signed and Sealed this

First Day of April, 2003

JAMES E. ROGAN
*Director of the United States Patent and Trademark Office*

UNITED STATES PATENT AND TRADEMARK OFFICE
CERTIFICATE OF CORRECTION

PATENT NO.    : 6,096,872
DATED         : August 1, 2000
INVENTOR(S)   : Van Holten et al.

Page 1 of 1

It is certified that error appears in the above-identified patent and that said Letters Patent is hereby corrected as shown below:

<u>Title page,</u>
Item [75], Inventors, delete "Gilbert J. Quinton, Belle Meade both of" and insert -- , -- after Flemington.

Signed and Sealed this

Fourteenth Day of September, 2004

JON W. DUDAS
*Director of the United States Patent and Trademark Office*